US012599908B2

(12) United States Patent
Zhang et al.

(10) Patent No.: US 12,599,908 B2
(45) Date of Patent: Apr. 14, 2026

(54) APPARATUS AND METHODS FOR MULTIPLEXED AMPLIFICATION AND DETECTION OF DNA USING CONVECTIONAL HEATING AND LABEL-FREE MICROARRAY

(71) Applicant: William Marsh Rice University, Houston, TX (US)

(72) Inventors: David Yu Zhang, Houston, TX (US); Dmitriy A. Khodakov, Houston, TX (US); Xuemeng Zhang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 1044 days.

(21) Appl. No.: 17/276,098

(22) PCT Filed: Sep. 13, 2019

(86) PCT No.: PCT/US2019/051057
§ 371 (c)(1),
(2) Date: Mar. 12, 2021

(87) PCT Pub. No.: WO2020/056292
PCT Pub. Date: Mar. 19, 2020

(65) Prior Publication Data
US 2022/0048033 A1 Feb. 17, 2022

Related U.S. Application Data

(60) Provisional application No. 62/731,495, filed on Sep. 14, 2018.

(51) Int. Cl.
B01L 7/00 (2006.01)
B01L 9/00 (2006.01)
C12Q 1/686 (2018.01)

(52) U.S. Cl.
CPC ................. B01L 7/525 (2013.01); B01L 9/52 (2013.01); B01L 2200/04 (2013.01);
(Continued)

(58) Field of Classification Search
CPC ........ B01L 7/525; B01L 9/52; B01L 2200/04; B01L 2200/0663; B01L 2200/0689;
(Continued)

(56) References Cited

U.S. PATENT DOCUMENTS 6,159,368 A * 12/2000 Moring ............... B01L 3/50255
422/258
2004/0248287 A1* 12/2004 Hu .......................... B01L 3/508
435/287.2
(Continued)

FOREIGN PATENT DOCUMENTS

CN 105802848 A 7/2016
KR 1020170054393 A 5/2017
(Continued)

OTHER PUBLICATIONS

English translation of First Office Action issued in Chinese Patent Application 201980067896.6, dated Jun. 6, 2022.
(Continued)

*Primary Examiner* — Jill A Warden
*Assistant Examiner* — Jacqueline Brazin
(74) *Attorney, Agent, or Firm* — pH IP Law

(57) ABSTRACT

The disclosure describes apparatus and methods for multiplexed amplification and detection of nucleic acid targets in a sample. Embodiments of the present disclosure include a mechanical system configured to provide loading, vertical positioning and clamping of a chip; a thermal control system configured to maintain distinct temperatures of the chip, and an optical fluorescence imaging system.

18 Claims, 22 Drawing Sheets

(52) U.S. Cl.
CPC ................. *B01L 2200/0663* (2013.01); *B01L 2200/0689* (2013.01); *B01L 2200/147* (2013.01); *B01L 2300/027* (2013.01); *B01L 2300/1805* (2013.01); *C12Q 1/686* (2013.01)

(58) Field of Classification Search
CPC ......... B01L 2200/147; B01L 2300/027; B01L 2300/1805; B01L 3/502715; B01L 9/527; B01L 2300/0816; B01L 2300/0822; B01L 2300/088; B01L 2400/0445; C12Q 1/686; C12Q 2537/143; G01N 21/6458
USPC ...................................................... 435/287.2
See application file for complete search history.

(56) References Cited

U.S. PATENT DOCUMENTS

| | | | |
|---|---|---|---|
| 2006/0160205 A1 | 7/2006 | Blackburn et al. | |
| 2007/0113880 A1 | 5/2007 | Atwood et al. | |
| 2008/0032295 A1* | 2/2008 | Toumazou ......... | G01N 27/4145 |
| | | | 435/287.2 |
| 2008/0075380 A1* | 3/2008 | Dube ..................... | G01N 21/64 |
| | | | 382/255 |
| 2010/0267127 A1 | 10/2010 | Chung et al. | |
| 2011/0312697 A1 | 12/2011 | Facer et al. | |
| 2012/0046203 A1 | 2/2012 | Walsh et al. | |
| 2017/0176479 A1 | 6/2017 | Lüdicke et al. | |
| 2017/0183713 A1 | 6/2017 | DeJohn et al. | |
| 2018/0099279 A1 | 4/2018 | Bruckmann et al. | |
| 2018/0147573 A1 | 5/2018 | Hiddessen et al. | |

FOREIGN PATENT DOCUMENTS

| | | | | |
|---|---|---|---|---|
| WO | WO 1997022882 | * | 6/1997 | |
| WO | WO-0025113 A1 | * | 5/2000 | ........ G01N 21/6452 |
| WO | WO 2017/066485 | | 4/2017 | |
| WO | WO 2017/172760 | | 10/2017 | |
| WO | WO-2017172760 A1 | * | 10/2017 | ........... B01L 3/5027 |

OTHER PUBLICATIONS

Extended European Search Report issued in European Patent Application No. 19861221.0, dated May 2, 2022.
First Examination Report issued in Australian Patent Application No. 201933853, dated Nov. 4, 2022.
Kusuma, B. R. et al.,"Synthesis and Evaluation of Novologues as C-Terminal Hsp90 Inhibitors with Cytoprotective Activity against Sensory Neuron Glucotoxity," *Journal of Medicinal Chemistry*, 55 (2012): 5797-5812.
PCT International Preliminary Report on Patentability Opinion issued in International Patent Application No. PCT/US2019/051057, dated Mar. 25, 2021.
PCT International Search Report and Written Opinion issued in International Patent Application No. PCT/US2019/051057, dated Jan. 9, 2020.
Office Action issued in Japanese Application No. 2021-514009, and English translation thereof, mailed Aug. 14, 2023.
Decision of Patent Grant for Korean Application No. 10-2021-7009737, dated Jun. 3, 2025, 8 Pages (7 Pages of Official Copy and 1 Page of English Translation).
Office Action issued in Japanese Application No. 2021-514009, mailed Oct. 10, 2024.
Office Action issued in Korean Application No. 10-2021-7009737, mailed Nov. 28, 2024, and English translation thereof.

\* cited by examiner

417 Claw for fixing
Press Bar

412

417   Claw for fixing
Press Bar

411

Claw for fixing 414
Press Bar b

Claw for fixing
Press Bar
427

420

427 Claw for fixing
Press Bar

422

421

C d   500 c   500 e f 610  600 g

APPARATUS AND METHODS FOR MULTIPLEXED AMPLIFICATION AND DETECTION OF DNA USING CONVECTIONAL HEATING AND LABEL-FREE MICROARRAY

CROSS-REFERENCE TO RELATED APPLICATIONS

This application is a national phase application under 35 U.S.C. § 371 of International Application No. PCT/US2019/051057, filed Sep. 13, 2019, which claims priority to U.S. Provisional Patent Application Ser. No. 62/731,495 filed Sep. 14, 2018, the entire contents of each of which are incorporated by reference herein.

The invention was made with government support under Grant No. R01 CA203964 awarded by the National Institutes of Health and the National Cancer Institute. The government has certain rights in the invention.

BACKGROUND

A. Field

This disclosure relates to apparatus and methods for multiplexed amplification and detection of DNA using convectional heating and a label-free microarray.

B. Related Art

There is a strong market demand for rapid and multiplexed DNA diagnostics from government agencies, hospitals and physician offices, and civilian consumers. Current commercial qPCR systems are large and expensive, and furthermore limited to simultaneous detection of 4-6 DNA markers of interest (4-6plex). Two examples of commercial qPCR systems that allow closed tube 20-plex analysis of a single DNA sample are Luminex xTag and Biofire FilmArray. Both systems require bulky (>20 kg) and expensive (>550,000) instruments, and are not suitable for point-of-care applications. Isothermal DNA amplification methods, such as Alere i Influenza assay, do not require large or complex instruments, but are limited to 3-plex. Finally, next-generation sequencing (NGS) allows extremely high multiplex analysis of DNA, but requires labor-intensive library preparation workflow (twelve hours or more) and long sequencing run (twenty-four hours or more). These labor and time-intensive qualities render NGS impractical for point-of-care applications. A comparison of different platforms based on their multiplexing capability and instrument affordability/portability is shown in FIG. 1. Embodiments related to the current invention (described as the "Donut PCR" platform discussed in more detail below) uniquely allows highly multiplexed DNA testing with an affordable and portable instrument.

International Patent Application No. PCT/US2017/02453 and PCT Patent Publication WO 2017/172760 ('760 Publication) disclose systems and methods developed by inventors of the pending application that enable highly multiplexed DNA analysis in a point-of-care setting. The systems disclosed in the '760 Publication will be referred to herein as the "Donut PCR system" (or similar terms) in reference to the circular nature of the embodiments. The '760 Publication disclose a Donut PCR consumable chip, a method for covalent attachment of the probe to the inner surface of the fluidic reaction chamber, PCR reagents comprising amplification primer, and detection probe design. In the '760

Publication, several different instruments were used for performing PCR amplification, microarray fluorescent imaging, image analysis and data interpretation. Furthermore, running the assay required numerous manual intervention steps. Here, a single unified instrument is disclosed that incorporates all mechanical, thermal, optical, and user-interface components, allowing a DNA sample-in answer-out platform.

There appear to be at least three application areas in which the highly multiplex and portable nature of the Donut PCR system uniquely filled unmet needs: (1) home- and pharmacy-based detection and subtyping of infectious diseases, (2) hospital bedside analysis of hospital-acquired infections, and (3) field-based agricultural and veterinarian genetic profiling and disease detection applications.

As previously mentioned, the '760 Publication discloses the Donut PCR assay and consumable chip. As used herein, the term "chip" includes convection flow fluidic devices as described in the '760 Publication. Although some necessary components of the instrument are described, the '760 Publication does not describe a fully integrated Donut PCR instrument in which no manual intervention is needed past the initial loading of the chip. In particular, it does not describe mechanical components needed for loading the Donut PCR chip and automated clamping of the chip to the heaters to form good thermal contacts. Additionally, the '760 Publication describes use of a fluorescence microscope and does not describe optical components (filters, lens, mirrors) needed for a standalone readout device. Consequently, the present invention is novel and inventive over the '760 Publication.

A large number of quantitative PCR (qPCR) instruments have been invented and commercialized by companies such as Applied Biosystems, Bio-Rad Laboratories, Qiagen, Cepheid, and Roche. These qPCR instruments all include an active cooling mechanism and is power intensive. Additionally, none of these qPCR instruments utilize a camera with pixel resolution less than 100 μm for image acquisition of fluorescence spots that is necessary for achieving high plex readout. Consequently, the present invention is novel and inventive over past qPCR instruments.

Convection PCR was reported in academic literature in 2002 and utilize two heaters at different temperatures. However, reported convection PCR instruments do not integrate a microarray for high plex DNA analysis, and consequently no reported convection PCR instrument utilize a camera with pixel resolution less than 100 μm for image acquisition of fluorescence spots that is necessary for achieving high plex readout. Consequently, the present invention is novel and inventive over past convection PCR instruments.

Microarrays use spatial separation of specific probes to achieve high plex readout for DNA analysis. However, commercial microarrays use active fluidics (e.g. pumps) and/or manual washes to remove unbound labeled reagents or amplicons, resulting in an open system prone to contamination. In contrast, the microarray embedded in the Donut PCR chip is mounted vertically in the present invention, and differentially heated to 95° C. and 60° C. using two separate heaters. Consequently, the present invention is novel and inventive over past microarray art.

SUMMARY

Briefly, the present disclosure provides apparatus and methods for multiplexed amplification and detection of nucleic acid targets in a biological sample. Embodiments of the present disclosure include a mechanical system configured to provide loading, vertical positioning and clamping of a chip; a thermal control system configured to maintain distinct temperatures of the chip, and an optical fluorescence imaging system.

Certain embodiments include an apparatus for multiplexed amplification and detection of nucleic acid targets in a sample, where the apparatus comprises: a mechanical system configured to provide loading, vertical positioning and clamping of a chip; a thermal control system configured to maintain a first temperature of the chip and a second temperature of the chip, wherein the first temperature is distinct from the second temperature; an optical fluorescence imaging system configured to collect spatial information in an array of at least 40 pixels×40 pixels; an electrical power system configured to provide electrical energy to the mechanical system, the thermal control system, and the optical fluorescence imaging system; a controller configured to control operation of the mechanical system, the thermal control system, the electrical power system, and the optical imaging system; and a graphical user interface (GUI) configured to allow a user to operate the control system via user interface software.

In particular embodiments, the chip has a height between 10 mm and 320 mm, a width between 10 mm and 320 mm, and a thickness between 0.5 mm and 10 mm. In some embodiments, the GUI is a touch-screen interface. In specific embodiments, the touch-screen interface is incorporated in a smartphone. In certain embodiments, the mechanical system comprises a chip holder, a frame, a sliding component, and a support component. In particular embodiments, the chip holder comprises an insertion slot, a positioning slot, and a motion control set. In some embodiments, the frame comprises a base, a main structural carrier, a press bar locator, a press bar, and a motion control set. In specific embodiments, the motion control set comprises a motorized moving component and its holder.

In certain embodiments, the motorized moving component comprises a linear actuator or a step motor. In particular embodiments, the sliding component comprises a sliding platform and a sliding bar. In some embodiments, the support component comprises a rail stand. In specific embodiments, the thermal control system comprises a plurality of temperature sensors, a plurality of heat blocks, and a heat source. In certain embodiments, the plurality of temperature sensors comprise a resistance temperature detector (RTD), a thermistor, a thermocouple, or an IR sensor. In particular embodiments, a temperature sensor of the plurality of temperature sensors is embedded into a heat block. In some embodiments, a temperature sensor of the plurality of temperature sensors is coupled to a surface of a heat block of the plurality of heat blocks. In specific embodiments, the plurality of heat blocks comprise aluminum, stainless steel, or brass.

In certain embodiments, the plurality of heat blocks collectively contact at least 50 percent of a total surface area of the chamber. In particular embodiments, the heat source comprises an adhesive flexible heater, a heat probe, or a heating wire. In some embodiments, the fluorescence imaging system comprises a light source, an optics module, and a detector with at least 40×40 pixels. In specific embodiments, the detector is a camera. In certain embodiments, the camera comprises a scientific camera or a smartphone camera. In particular embodiments, the light source comprises an arc lamp, a vapor lamp, a light-emitting diode (LED), or a laser. In some embodiments, the optics module comprises an excitation filter, a dichroic mirror, a beam splitter, an emission filter, a flat mirror, an objective, and/or an optical lens. In specific embodiments, the mechanical system comprises one or more plastics. In certain embodiments, the mechanical system comprises polylactic acid (PLA), polycarbonate (PC), acetonitrile butadiene styrene (ABS), or ceramics. In particular embodiments, the electrical power system comprises an AC/DC power source, a MOSFET, a switch, an amplifier, a diode, a transistor, and a resistor. In some embodiments, the controller comprises a microcontroller and/or a PID controller. In specific embodiments, the microcontroller comprises Raspberry Pi, Arduino, or Genuino.

Certain embodiments include a method for analyzing a sample in a chip using the apparatus as described herein (including for example, the apparatus of claim 1). In particular embodiments, the method comprises: loading a chip into the apparatus; operating the mechanical system to clamp the chip between a first heat block and a second heat block; heating the first heat block to a first temperature; heating the second heat block to a second temperature, wherein the second temperature is distinct from the first temperature; directing excitation light from a light source to a surface of the chip; detecting emitted light from the chip; and analyzing the emitted light from the chip.

Some embodiments further comprise generating a data report documenting an analysis of the light emitted from the chip. Specific embodiments further comprise unclamping the chip from between the first heat block and the second heat block. Certain embodiments further comprise unloading the chip from the apparatus. In particular embodiments, loading the chip comprises operating a motor for linear movement. In some embodiments, loading the chip comprises operating a mechanism configured to draw the chip into the apparatus. In specific embodiments, clamping the chip comprises operating a mechanism with a self-locking motor, a cam-follower combination, or a spring.

In certain embodiments, the first temperature is maintained at between 75° C. and 105° C. during operation. In particular embodiments, the second temperature is maintained at between 30° C. and 75° C. during operation. In some embodiments, the first and second temperatures are controlled by a microcontroller program that alters a heat source power based on feedback from a temperature sensor. In specific embodiments, the first and second temperatures are controlled by a proportional-integral-derivative (PID) controller. In certain embodiments, a first temperature sensor is embedded in the first heat block. In particular embodiments, a second temperature sensor is embedded in the second heat block. In particular embodiments, a first temperature sensor is coupled to the surface of the first heat block. In some embodiments, a second temperature sensor is coupled to the surface of the second heat block. In specific embodiments, the excitation light source forms an angle with the surface of the chip that is between 30° and 90°. In certain embodiments, detecting emitted light from the chip comprises operating a camera to acquire images continually with a frequency of no less than 1 image every 2 minutes.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

DETAILED DESCRIPTION OF THE INVENTION

Exemplary embodiments of the present disclosure comprise three main components: (1) chip: an annular reaction chamber for reliable convection PCR without require active cooling or fluidics, (2) assay and readout: simultaneous detection and analysis of 50 or more DNA targets using a single fluorescence channel via the spatial separation of probes in a microarray, in a closed tube manner, and (3) apparatus: a portable and affordable instrument that implements multiplexed amplification and real-time readout.

The principle of convection PCR is that aqueous solution can be controllably circulated as a result of temperature-induced density differences (Rayleigh-Benard convection). In short, warmer solutions are less dense, and colder solutions are more dense, the force of gravity can thus drive the circulation of a differentially heated solution. Because no active cooling or fluidics components are needed, the size and weight of convection PCR instruments will be significantly lower than conventional PCR that utilize Peltier systems.

Figure 1:
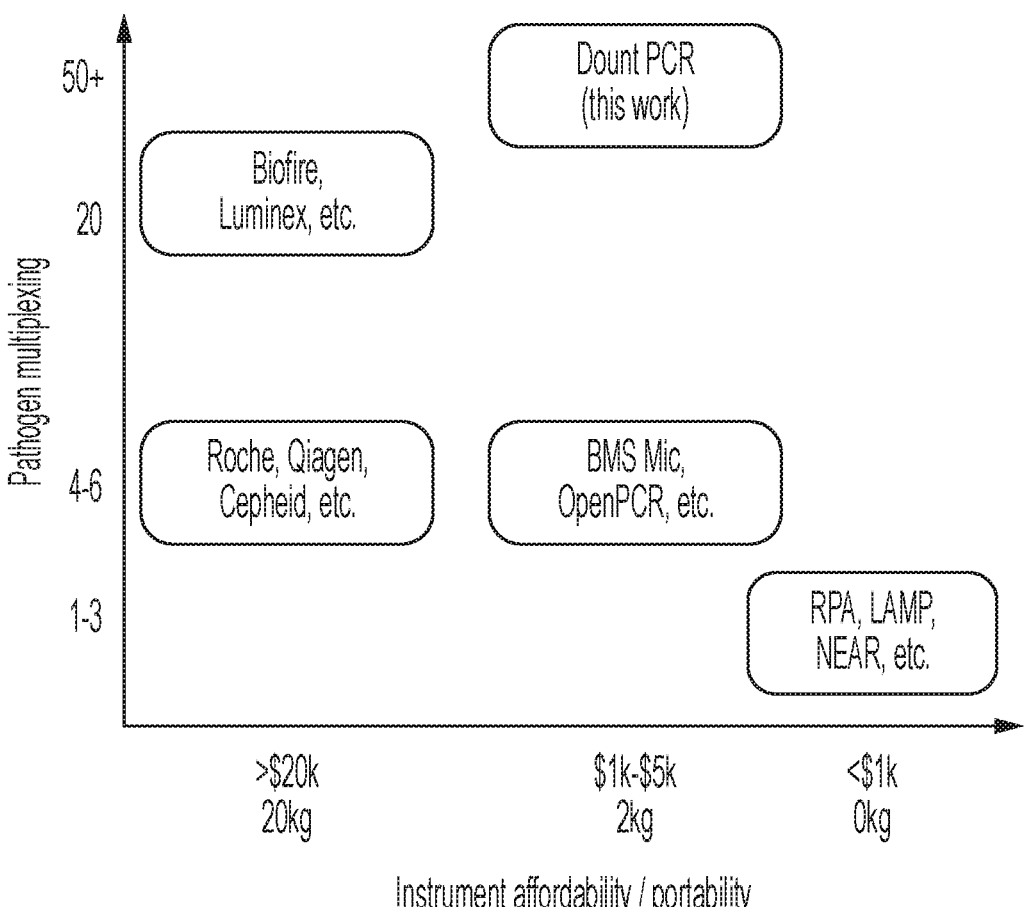
FIG. 1 is a graphical comparison of different platforms regarding their multiplexing capability and instrument affordability and portability.
Figure 2:
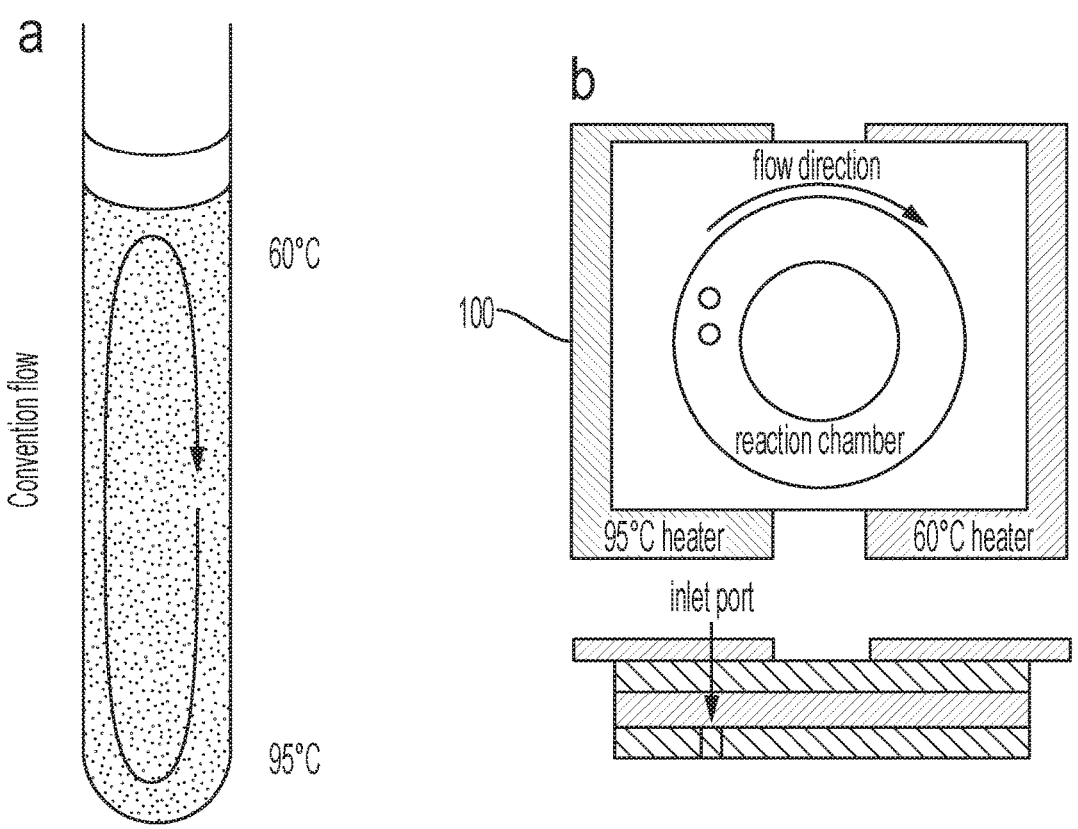
FIG. 2 illustrates convection flow in a capillary tube and flow in a chip according to the present disclosure, as well as associated manufacturing and operating principles.
Figure 2:
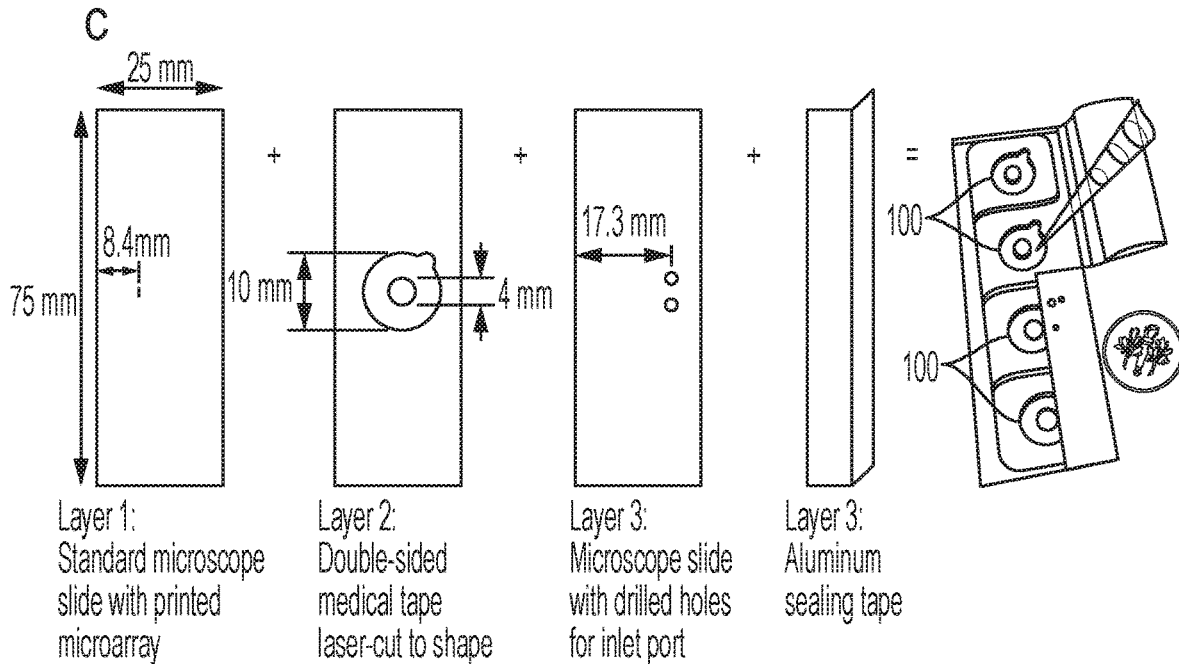
Figure 2:
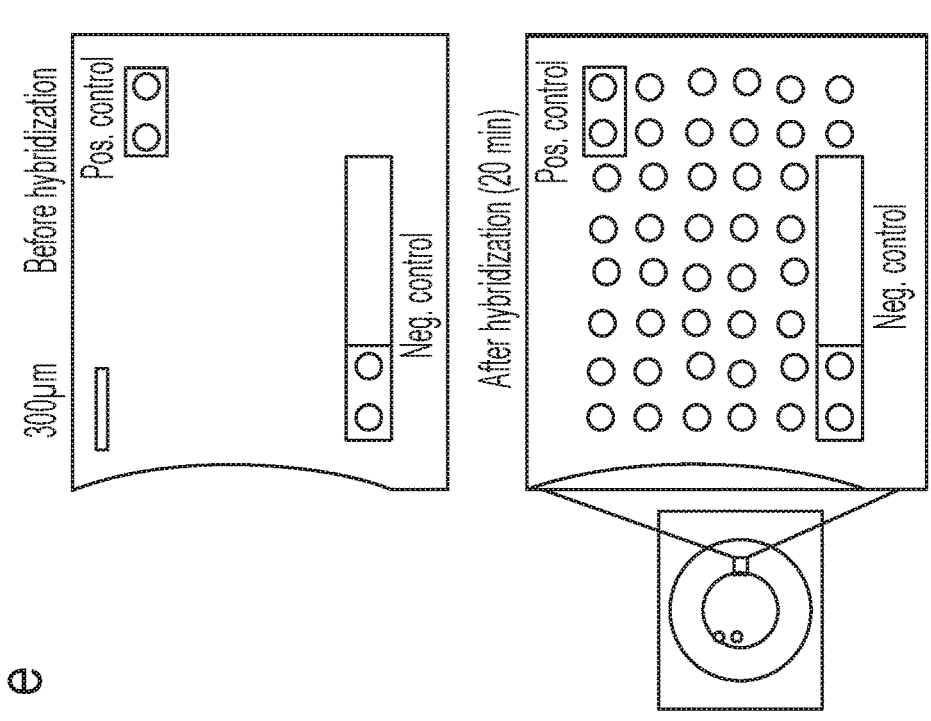
Figure 2:
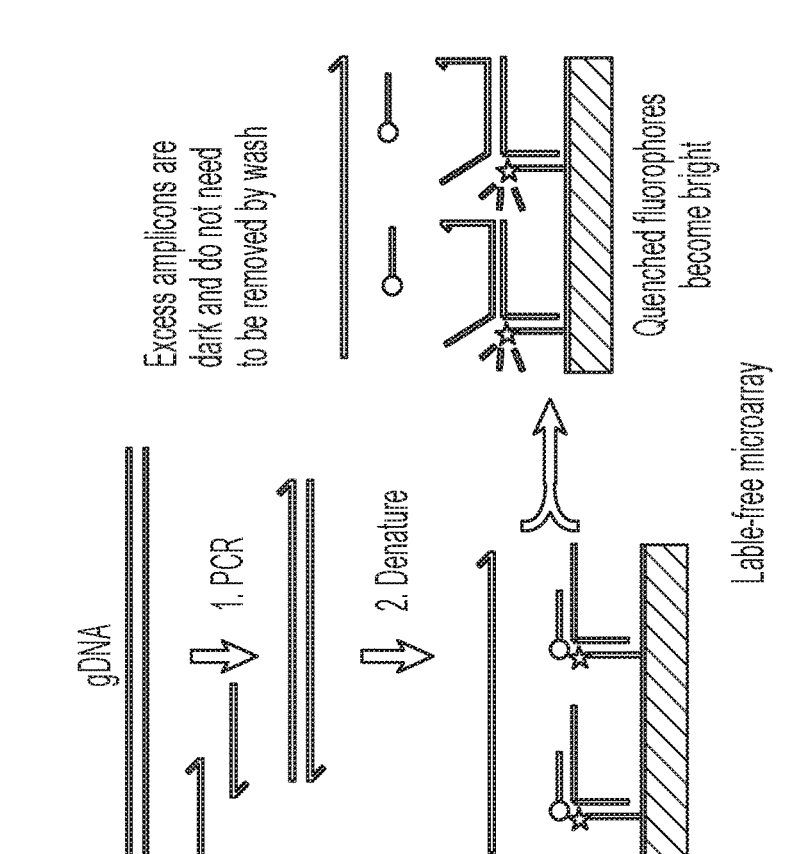

Convection PCR was firstly conceptually introduced and experimentally demonstrated in 2002, using vertical capillary tubes as the reaction chamber as shown in section A of FIG. 2. However, this reaction chamber has "dead zones" with low circulation speed, that result in nonspecific DNA amplification and primer dimer formation. These relative disadvantages of convection PCR using capillary tubes rendered convection PCR an unattractive alternative for conventional PCR, so there is poor commercial adoption. In contrast, the engineered annular reaction chamber shown in section B of FIG. 2 eliminates dead zones in the chip and facilitates uniform circulation of the PCR solution within the chamber through the 95° C. and 60° C. temperature zones. The Donut PCR fluidic chip 100 shown in section B is designed to achieve more uniform temperature control than the capillary tube, in order to enable convection PCR for diagnostics-grade DNA analysis. The PCR solution is injected into the reaction chamber via the inlet port, while the other port allows air bypass. The internal circular insert ("island") in the middle prevents dead space where the PCR mixture may dwell for extended periods of time at uncontrolled temperatures. The manufacturing and assembly process for Donut PCR chip 100 is shown in section C of FIG. 2. An overview of label-free microarray technology that may be used in conjunction with Donut PCR chip 100 is shown in section D of FIG. 2. The amplicons and dNTPs are unlabeled, and localized fluorescence increase is achieved through the displacement of a quencher-labeled oligonucleotide by the unlabeled amplicon. This technology thus avoids open-tube wash steps. Section E of FIG. 2 provides fluorescent images of the label-free microarray before (top) and after (bottom) hybridization to the amplicon mixture. The images here were taken using a Zeiss Axio Observer fluorescence microscope.

Conventional quantitative PCR (qPCR) instruments use different spectral wavelengths to achieve multiplexed analysis of different DNA targets. However, the number of non-overlapping visible wavelength fluorophores is limited to 5-6. For applications from infectious disease and antibiotics resistance profiling to agricultural genetic profiling, often more than twenty different targets must be detected. It is possible to perform sample splitting, e.g. by profiling twenty different DNA targets in a sample via four reactions each testing five targets. However, in practice this is cumbersome and sacrifices sensitivity when samples are limited. Microarrays use spatial separation to achieve high multiplexing using a single fluorescence wavelength, but require labor-intensive and open-tube wash steps to suppress florescence background. The complex microarray workflow renders traditional microarrays unsuitable for in vitro diagnostic (IVD) use. In contrast, the microarray printed on the inside surface of the annular Donut PCR chip is a label-free microarray, and does not require washes to remove excess amplicons or reaction reagents.

To perform multiplexed amplification and detection of many DNA targets in the Donut PCR chip requires that the chip to be light mounted tightly against two heaters at different temperatures in order to form a good thermal contact. The Donut PCR chip needs to be moved to a dark space or a chip-loading door must be sealed, in order to prevent excess background light. The Donut PCR chip also needs to be illuminated with light of the proper wavelength, intensity, and focus through the use of properly selected and positioned filters and optics. A camera takes pictures of the microarray at regular intervals, and then software is used to interpret the images to make calls on the presence/absence of a bright spot. Exemplary embodiments of the present disclosure provide an integrated apparatus that achieves each of the processes described above.

Figure 3:
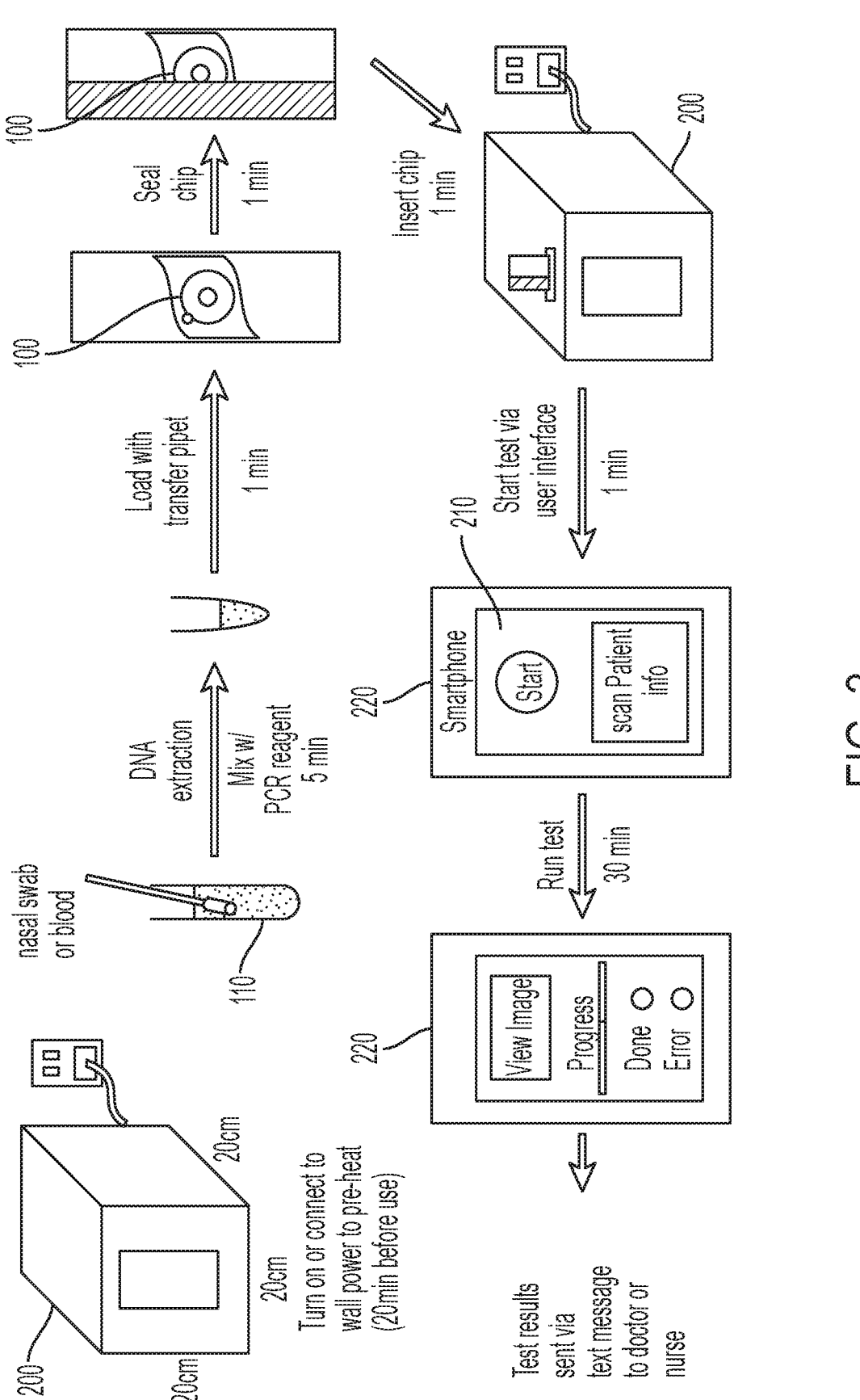
FIG. 3 illustrates workflow diagram for operation of an apparatus according to the present disclosure.

Referring now to FIG. 3, a schematic of an apparatus 200 for multiplexed amplification and detection of nucleic acid targets in a sample is provided, along with an overview of a workflow diagram for use with apparatus 200. As shown in FIG. 3, a sample 110 can be mixed with one or more PCR reagents and then loaded into chip 100 via a transfer pipette. Chip 100 (with sample 110) can then be sealed and inserted into apparatus 200 for analysis. A user can control operation of apparatus 200 via a graphical user interface (GUI) 210. In certain embodiments, GUI 210 can be wirelessly coupled to apparatus 200, and in particular embodiments, GUI 210 may be incorporated into a mobile device 220 (including for example a smartphone, laptop computer, tablet or other appropriate device). GUI 210 can be used to initiate analysis of sample 110 via apparatus 200 and display image results. Device 220 can be used to send test results to a doctor, nurse, or other healthcare professional.

Figure 4:
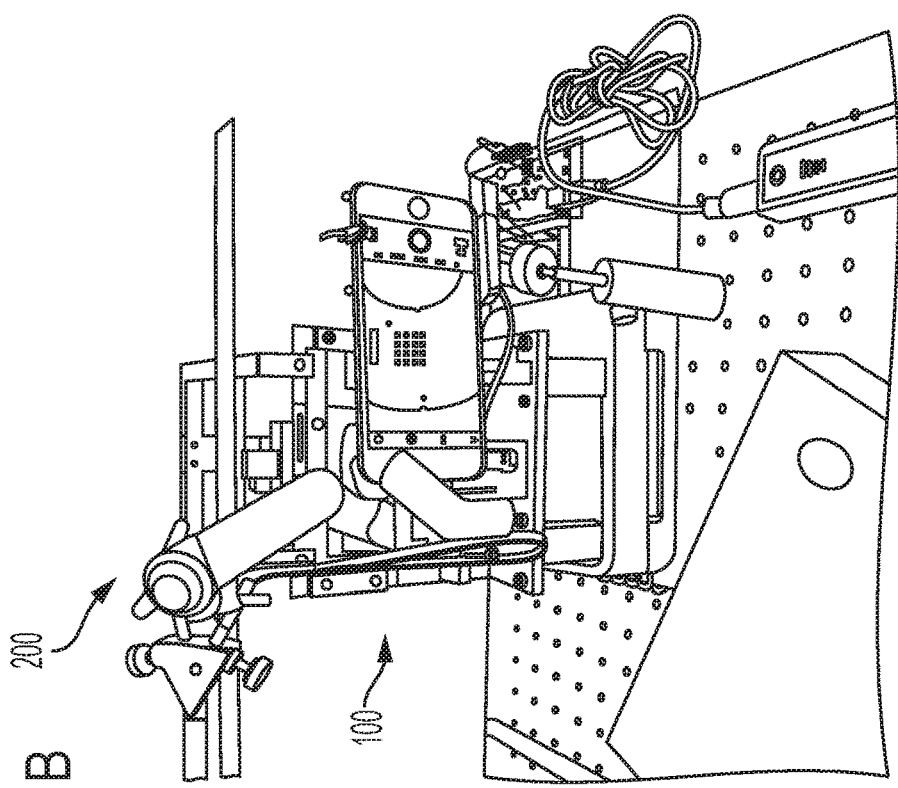
FIG. 4 illustrates a partially exploded view of an apparatus according to the present disclosure, as well as a photograph of a prototype apparatus and imaging results from the prototype.
Figure 4:
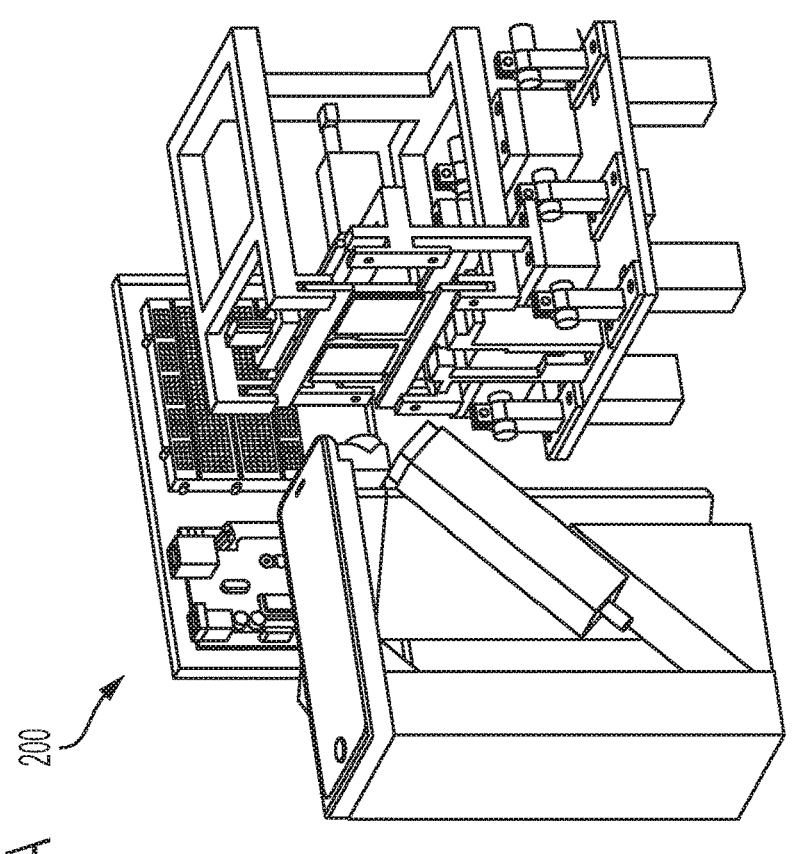

Referring now to FIG. 4, an overview of apparatus 200 is provided. Section A of FIG. 4 illustrates a 3-D diagram of assembled components (with the exception of the exterior housing). FIG. 4 section B provides a photograph of an engineering prototype of apparatus 200 (again, except for the exterior housing). Section C of FIG. 4 shows a fluorescence image of a 100-spot array in the Donut PCR chip 100, imaged by the embodiment of apparatus 200 shown in section B. Certain embodiments of apparatus 200 may comprise structural components that are 3-D printed (e.g. using a suitable device such as Ultimaker 3). Other components may include modules that are widely available off-the-shelf. In the embodiment shown in section B, a smartphone serves as the camera, image processing unit, user interface, and wireless data transmitter. The embodiment shown in FIG. 4 is wall-powered, but also has an internal power bank, that is intended to power up to 60 minutes of operation (e.g. one full sample analysis plus a margin for extra time that may be needed).

Figure 5:
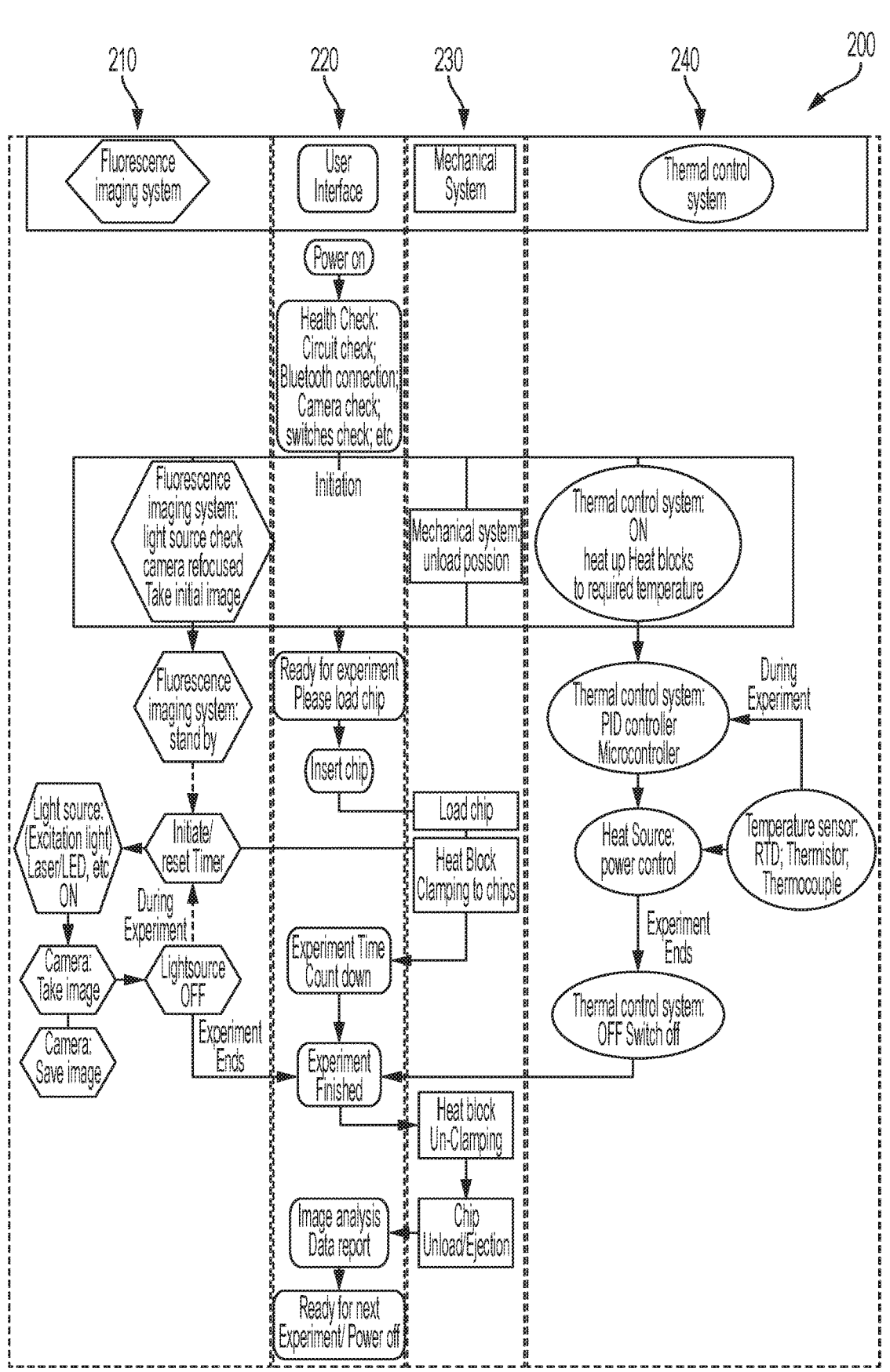
FIG. 5 illustrates a conceptual functional flowchart of an apparatus according to the present disclosure.

FIG. 5 provides a conceptual diagram or flowchart of an analysis performed by apparatus 200, which comprises steps executed in four major systems: fluorescence imaging 210, user interface 220, mechanical 230, and thermal control 240. An overview of a generic process for operating apparatus 200 is provided below in conjunction with a Donut PCR chip 100 loaded with the proper sample, dNTP, DNA polymerase, and buffer reagents.

A user can initially turn the power on to apparatus 200, so the system checks (verifying the controller is connected, checking camera functionality and light source illumination, etc.) is performed before initialization. During in initialization of apparatus 200, the thermal control system is turned on, then heating of the heat blocks to predetermined temperatures and maintaining them at the stabilized temperatures is activated. A more detailed temperature control method information will be explained further in the thermal control system section. Along with the heating block process, the temperature recording can also start simultaneously. The thermal control system can operate continuously until the experiment completes. System initialization process also comprises turning the fluorescence imaging system on, checking light source energy power, confirmation of the camera focus, and reassuring that the initialization image is ready to be taken for records. Next the system resets positions of the moving mechanical parts. This can include, for example, moving back the frame that holds heat blocks to an un-clamped position, setting up the chip holder to an un-load/ejection position and preparing to load chips.

Apparatus 200 can include a display indicating the apparatus is ready for the experiment or analysis. The user can then prepare the chip for loading into apparatus 200. Next, the user can insert and load the chip, ensuring the chip is loaded and positioned. Apparatus 200 can be configured so that the heat blocks will then clamp the chip. Apparatus 200 then indicates it is ready to start and displays a countdown for experiment/analysis. Apparatus 200 then initiates/resets the fluorescence imaging system timer, using the camera to take one image at a predefined interval (e.g. every 45 seconds). After each predefined interval, the light source will turn on in order to excite the fluorophores in the chip. In certain embodiments, lasers or LED lights with excitation filters can be considered as potential light sources.

Apparatus 200 can then use the camera to capture and save a fluorescent image of the current chip. Different types of fluorophores and instrument designs will require different fluorescence filter sets. Next, the light source power can be turned off and the next image can be taken at the predefined interval. This can be repeated until the experiment/analysis is completed. Upon experiment completion, the thermal control system and fluorescence imaging system will switch off. After finishing the analysis, the chip is automatically ejected. Users should be cautious due to the high temperature of the chip. The heat block in mechanical system can then be unclamped, and the chip then ejected. Apparatus 200 can continue analyzing images and finalizing the data report. The user can then continue to the next experiment or power apparatus 200 off.

Figure 6:
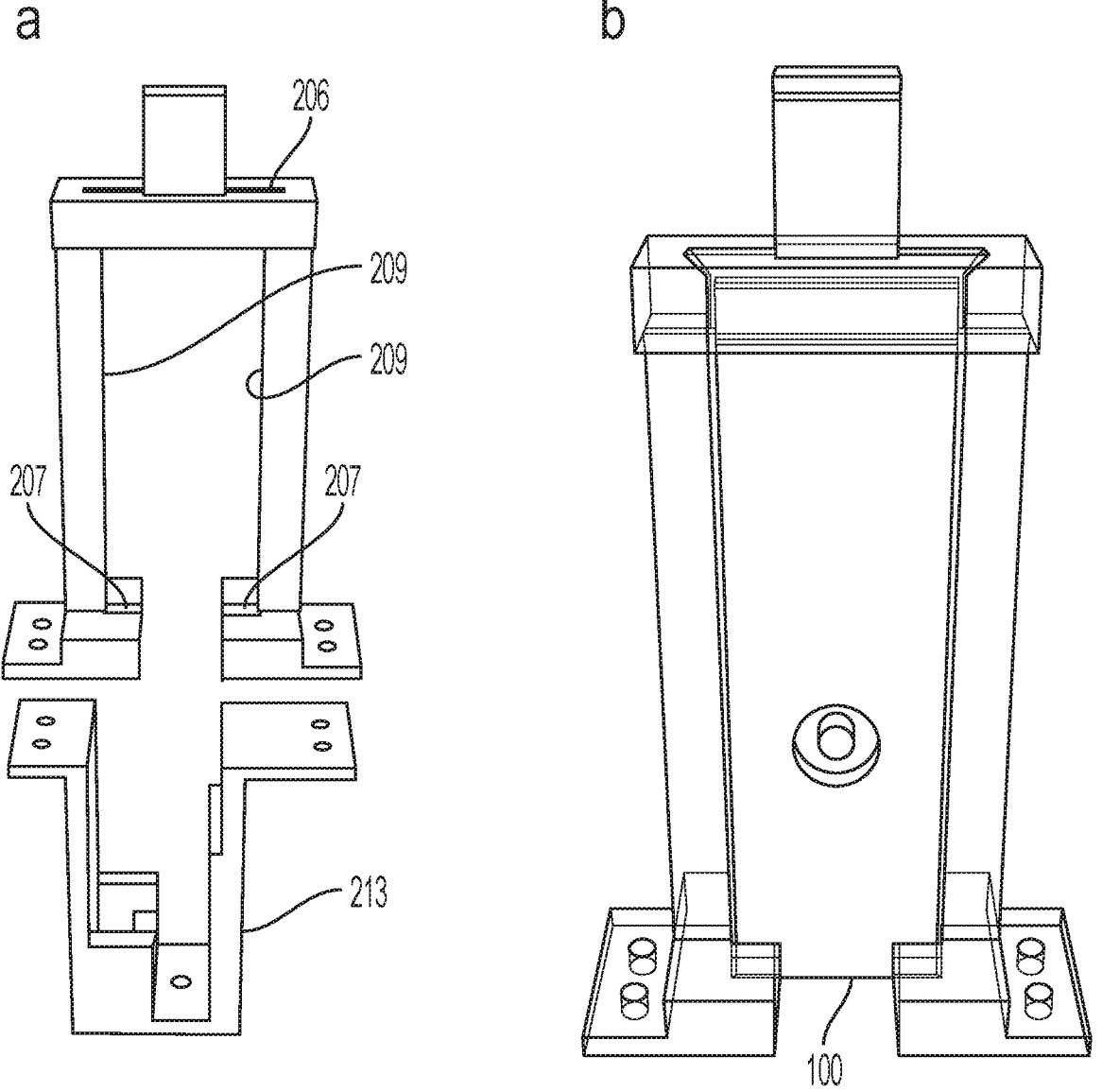
FIG. 6 illustrates perspective and photographic representations of a chip holder and chip of an apparatus according to the present disclosure.
Figure 6:
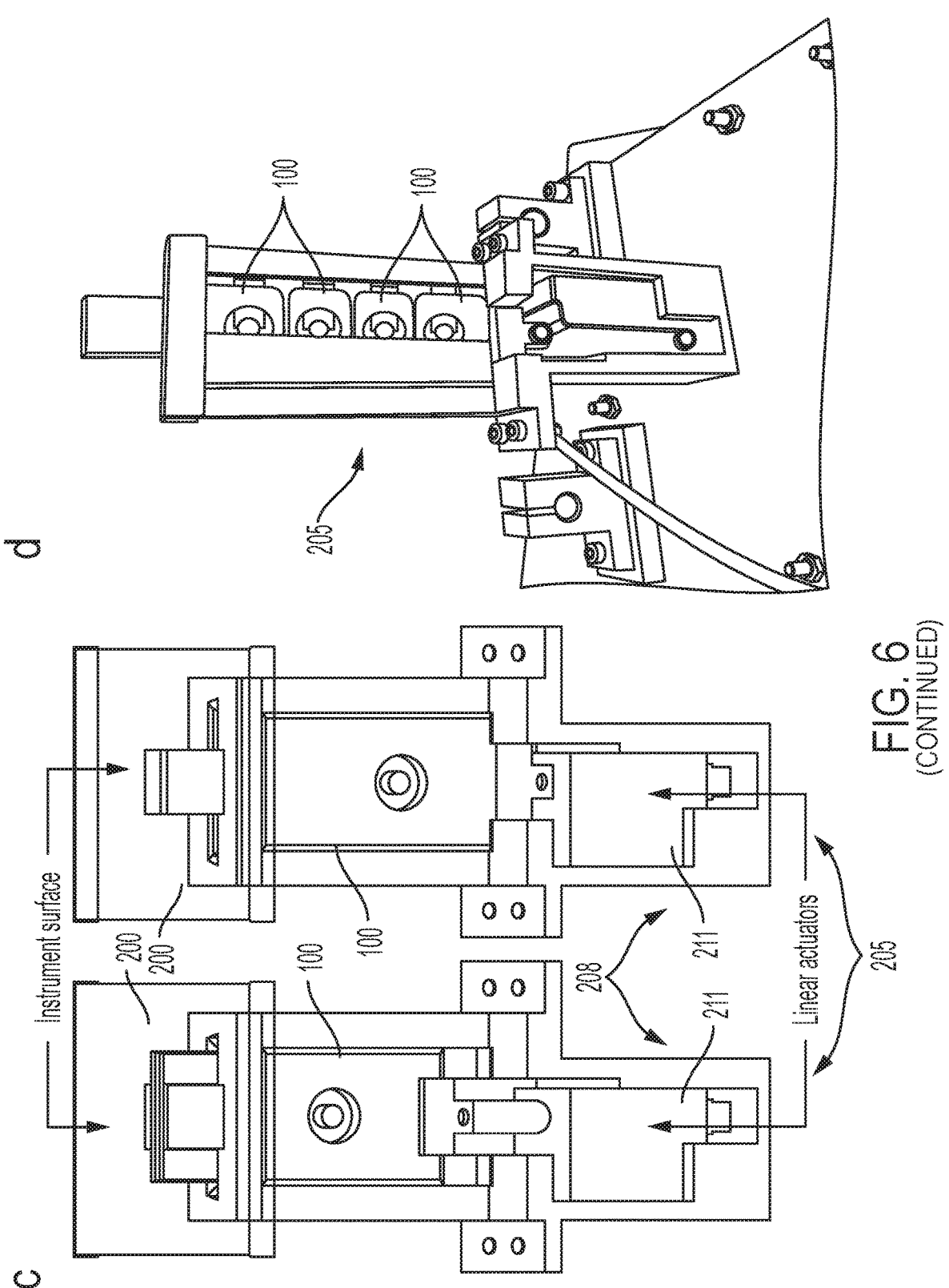

Referring now to FIG. 6, section A illustrates a 3-D diagram of the chip holder 205 configured to hold one or more chips 100. FIG. 6 section B demonstrates the position of chip 100 after loading into holder 205, while section C illustrates chip 100 in an unloaded position (left) and a loaded position (right). FIG. 6 section D provides a photograph of chip holder 205 (in this example manufactured via 3-D printing) loaded with chip 100.

Apparatus 200 includes components in a mechanical system that will perform functions including, but not limited to, chip loading and heat blocks clamping.

The function of chip holder 205 in apparatus 200 is to insert Donut PCR chip 100 and to guide the chip to move vertically to a predetermined position. The chip holder comprises three major parts: insertion slot 206, locating slot 207, and motion control sets 208. Insertion slot 206 is extruded out of the instrument surface for chip insertion. Chip 100 is inserted into insertion slot 206, which will support chip 100 to move up and down vertically, along with the guidance of motion control sets 208, chip 100 is then precisely be positioned in the locating slot 207.

Two vertical bars beside locating slot 207 act as guide rails 209 and are used as guidance to move chip 100 vertically up and down. Motion control sets 208 comprise two parts, the moving component 211 and its fixture 213. In certain embodiments, moving component 211 utilizes linear motion motors, for example, linear actuator or step motors. Fixture 213 of motion control set 208 is used for fixation and to insure stabilization of moving component 211 during chip 100 movement. Insertion slot 206, locating slot 207, guide rails 209, and fixture 213 collectively form integrated chip holder 205. In exemplary embodiments, moving component 211 of motion control set 208 is assembled on chip holder 205. After assembling entire chip holder 205 and moving component 211, they will be fixed inside apparatus 200. The process of vertical movement of chip 100 is guided and instructed by motion control sets 208, where Donut PCR chip 100 is the object that is being moved vertically.

Before the experiment, chip holder 205 is reset to an unloaded position, and moving component 211 (e.g. the linear actuator) will elongate as shown in the left view of FIG. 6 section C. After inserting chip 100, the chip will move down vertically along with the shortened linear actuator until chip 100 is positioned precisely in locating slot 207. At that time, both the upper edge and lower edge of chip 100 will be fitted in the insertion slot 206 (part of the lower edge of a chip 100) and locating slot 207 and stay vertically, as shown in FIG. 6 section D and section C right view. After the experiment, moving component 211 will elongate, and direct chip 100 to move upwards in order to eject chip 100.

In other embodiments (not shown) the chip holder may include different shapes to accommodate different types equipment. In particular embodiments, the chip holder may move vertically up and down, instead of moving only the chip itself.

Before an experiment or analysis is performed, chip holder 205 will be driven by moving component 211, and it will push insertion slot 206 out of apparatus 200 for chip insertion. After inserting chip 100, chip 100 will directly touch the bottom of locating slot 207, and the upper edge of the chip will be parallel to insertion slot 206. Moving component 211 will then drive the whole chip holder 205 to move downwards, and then pull the part of insertion slot 206 back to apparatus 200 and complete the process of chip loading.

After the experiment, moving component 211 will move upwards with the chip holder 205 that carries chip 100 to extrude insertion slot 206 out of the surface of instrument 200, and chip 100 then can be removed.

Figure 7:
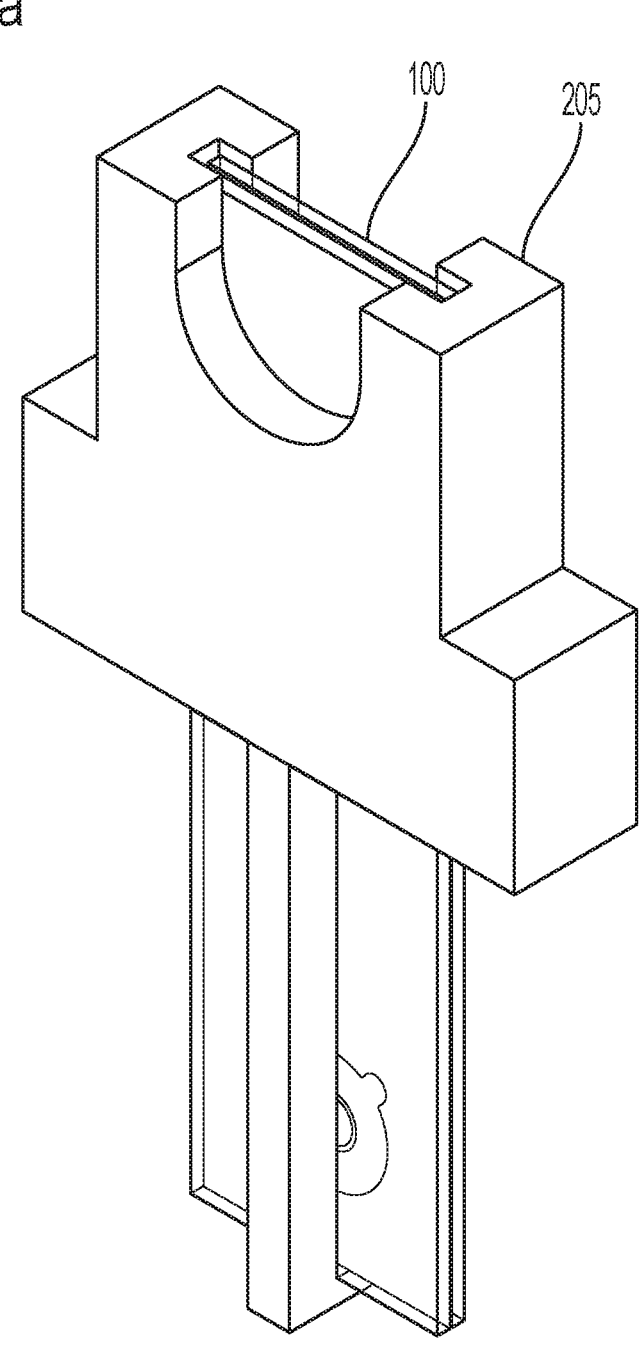
FIG. 7 illustrates schematic representations of alternative chip holders, loading mechanisms, and clamping mechanisms of an apparatus according to the present disclosure.
Figure 7:
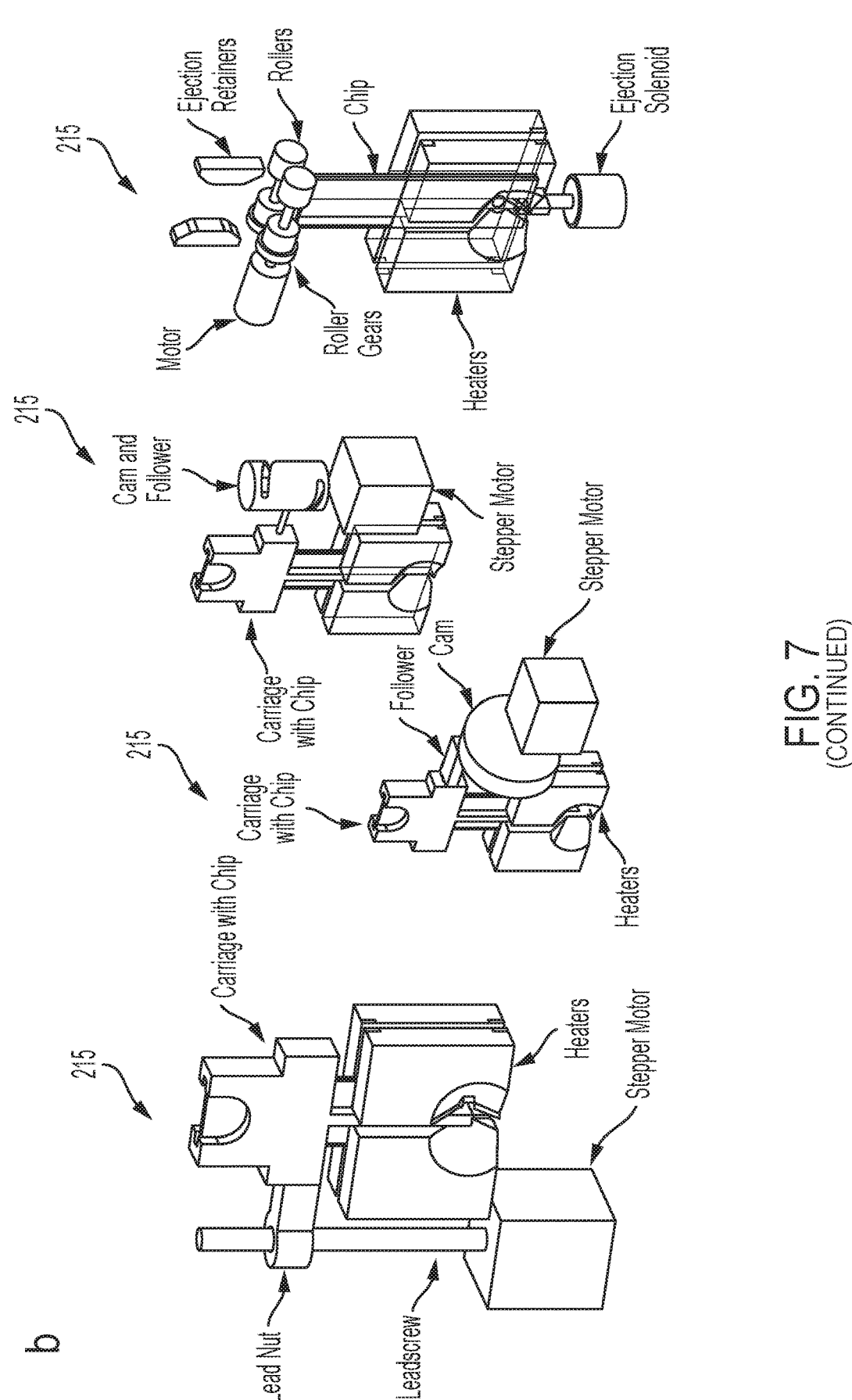
Figure 7:
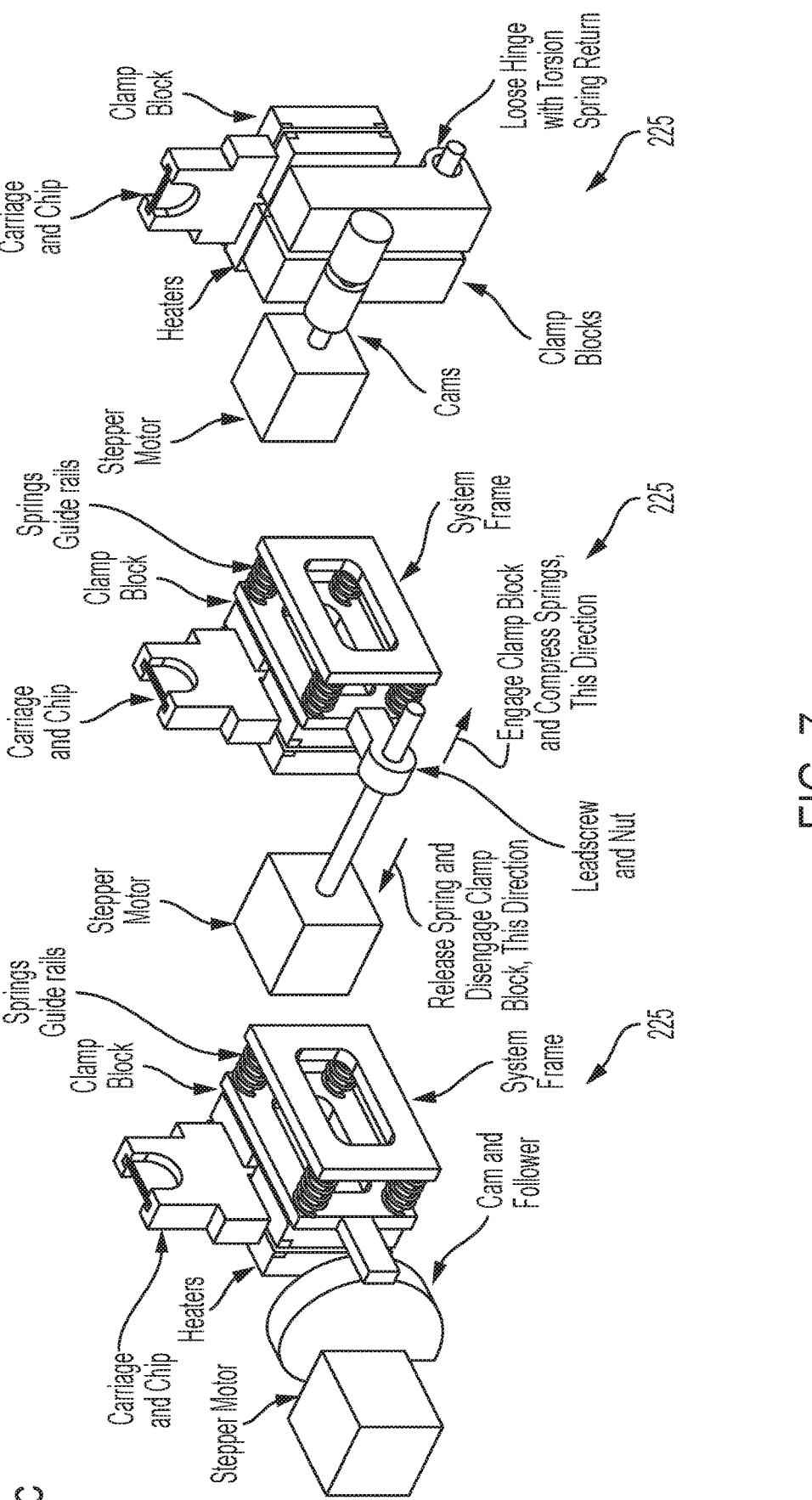

FIG. 7 section A illustrates an alternative design for chip holder 205 configured to hold chip 100. Section B of FIG. 7 provides four different configurations for a loading mechanism 215 configured to load chip holder 205. Each embodiment comprises heaters, but includes different components for moving chip holder 205 into and out of position between heaters. The first embodiment includes a stepper motor with a lead screw and a lead nut. The second embodiment includes a stepper motor with a cam rotating around a horizontal axis to raise and lower a follower coupled to the chip holder. The third embodiment includes a stepper motor with a cam rotating around a vertical axis to raise and lower a follower coupled to the chip holder. The fourth embodiment includes a motor coupled to roller gears and rollers configured to engage and raise and lower chip holder 205. FIG. 7 section C illustrates three different embodiments of clamping mechanisms 225 configured to clamp the heaters on each side of the chip holder and chip. Each embodiment includes a stepper motor configured to control movement of the components, and a clamp block configured to contact the heaters. The first embodiment includes a cam coupled to the stepper motor and a follower coupled to the clamp block. This embodiment also includes a plurality of springs on guide rails, where the springs are biased to exert a force on the clamp block toward the heaters (e.g. spring biased toward a clamped position). As the cam rotates, it can engage the follower and counteract the spring force to direct the clamp block away from the heaters (e.g. to an unclamped position).

The second embodiment in FIG. 7 section C illustrates a clamping mechanism 225 with a similar configuration to the previously described embodiment. However, instead of a cam, this embodiment utilizes a leadscrew and lead nut arrangement to move the clamp block toward and away from the heater. The third embodiment shown in FIG. 7 section C illustrates a clamping mechanism 225 with a stepper motor and cams that engage clamp blocks that pivot around a hinge mechanism. This embodiment also comprises a torsion spring configured to bias the pivoting clamp blocks toward the heaters.

Figure 8:
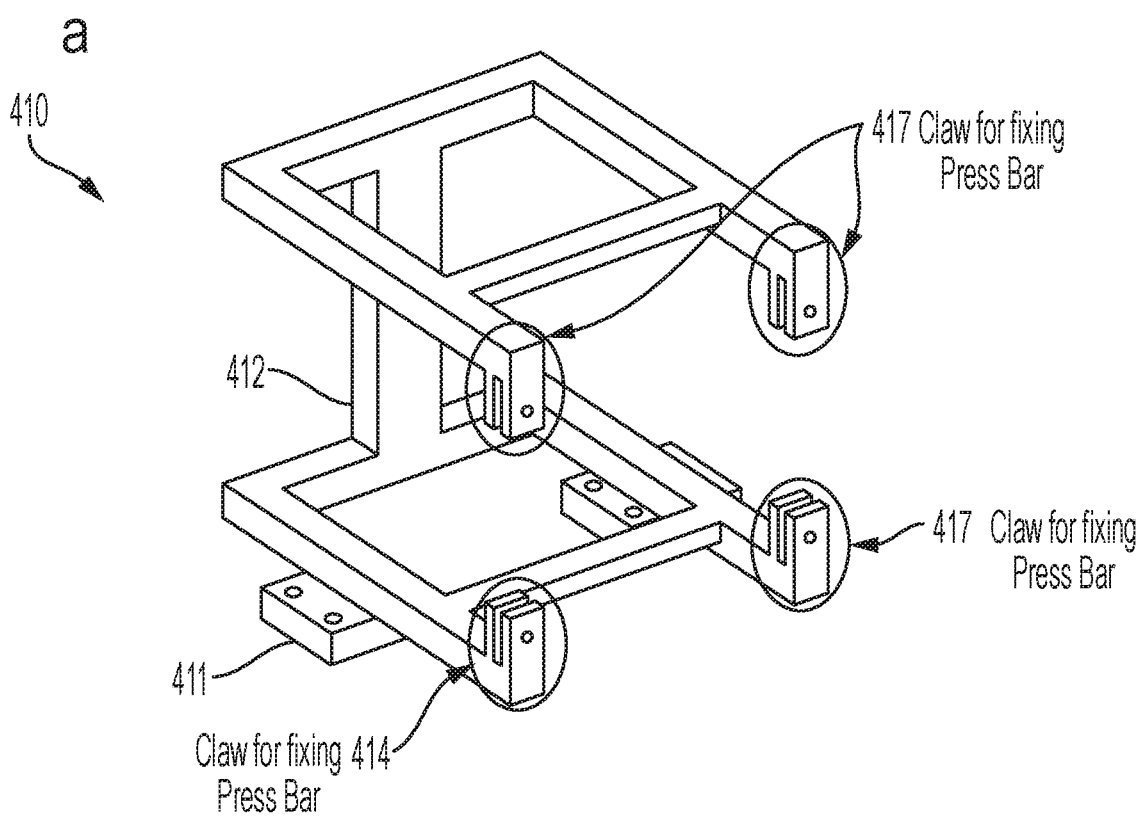
FIG. 8 illustrates perspective representations of individual sub-frames and an assembled frame of an apparatus according to the present disclosure.
Figure 8:
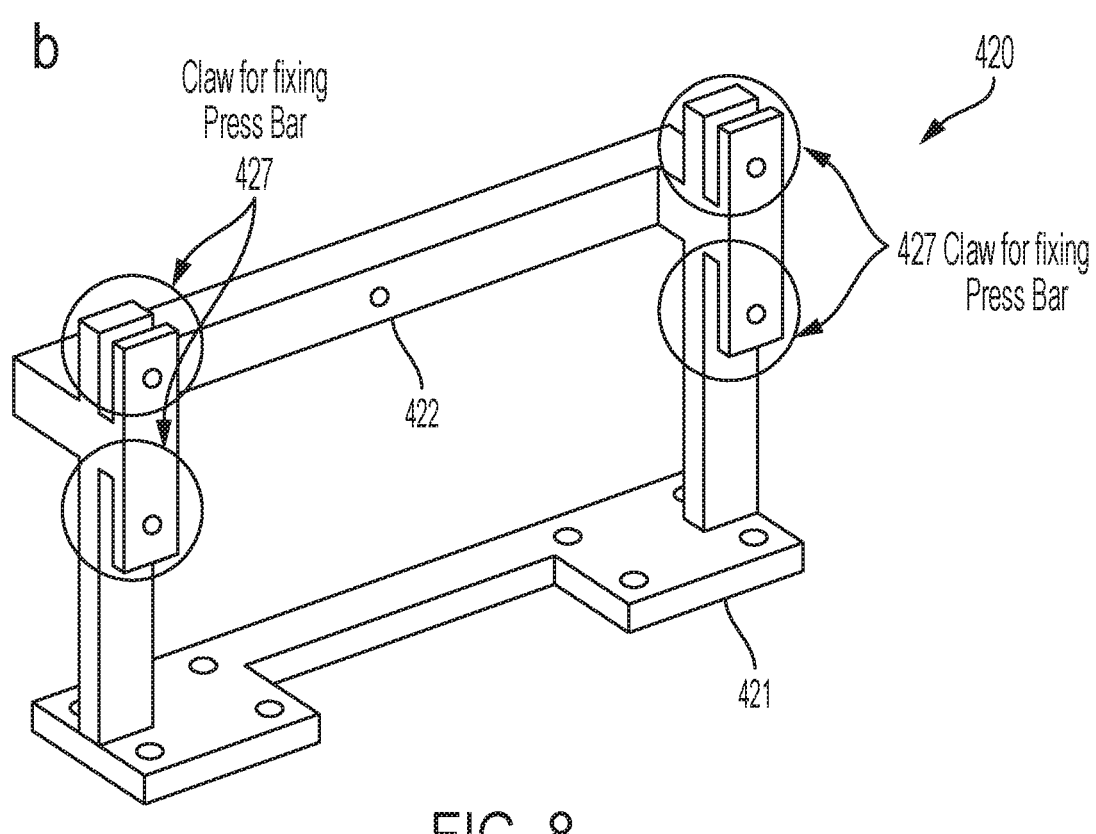
Figure 8:
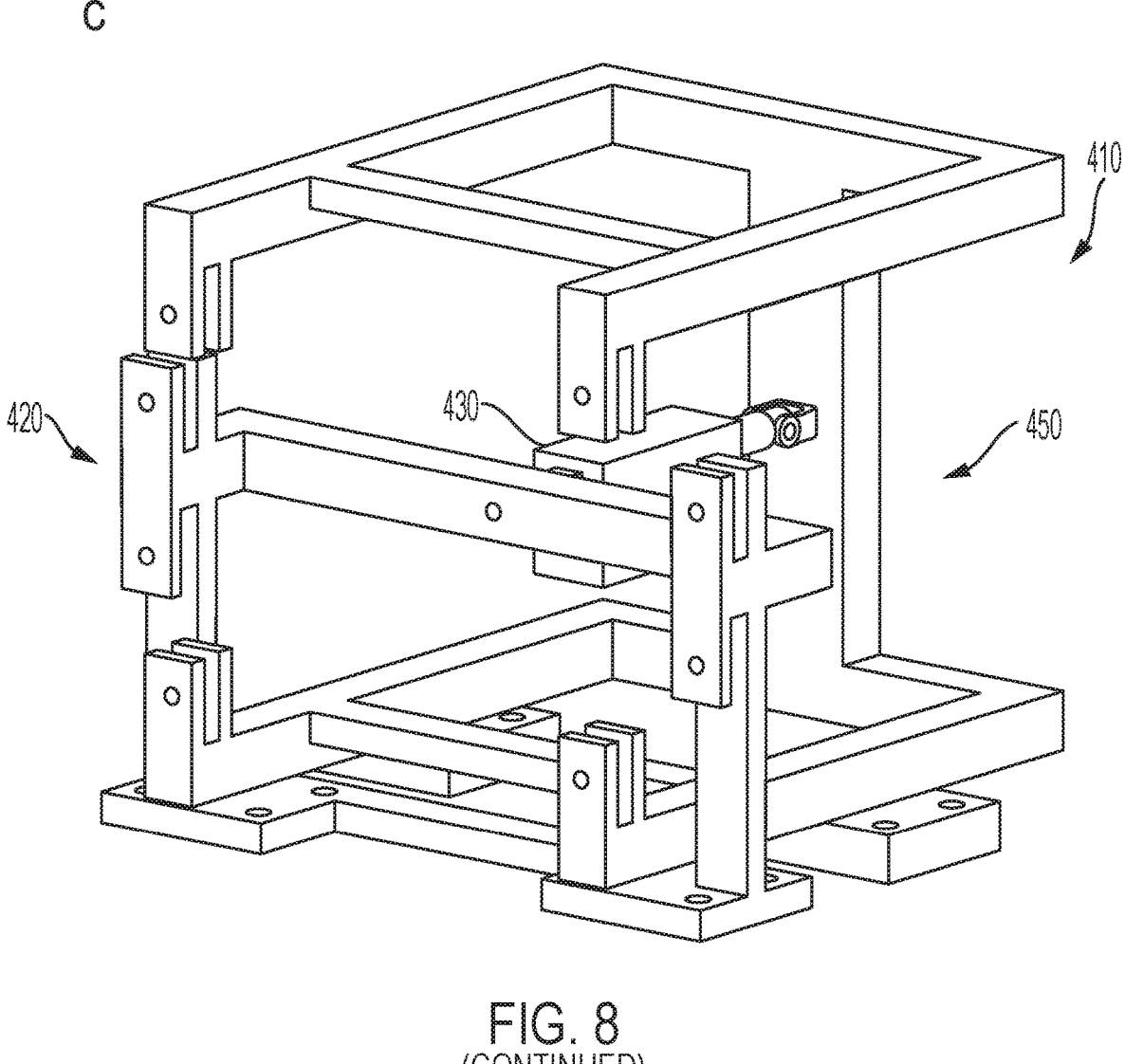
Figure 9:
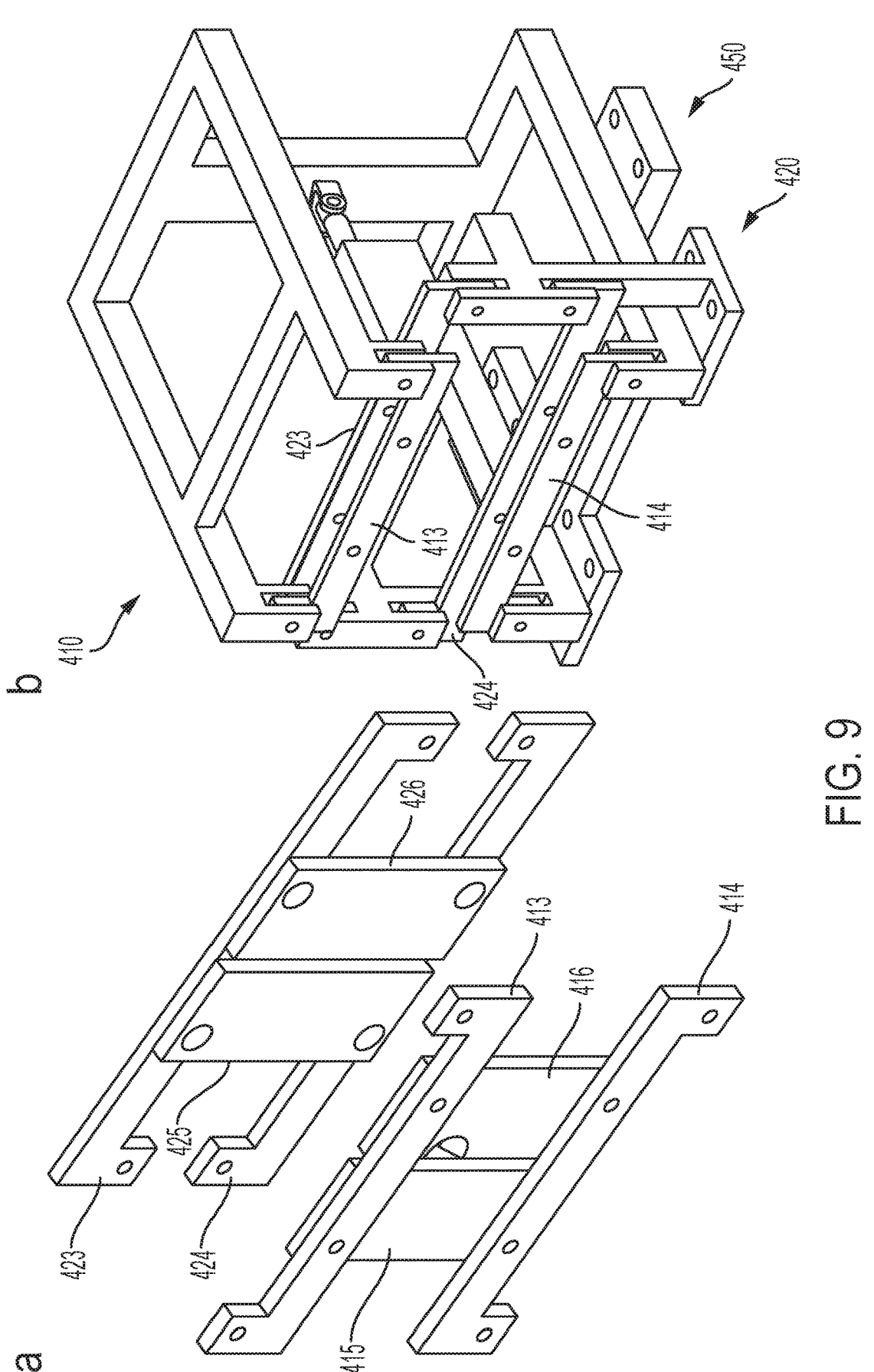
FIG. 9 illustrates perspective representations of press bars and an assembled frame of an apparatus according to the present disclosure.

Referring now to FIGS. 8 and 9, perspective views of individual and assembled frames are shown. A primary function of the frame is to vertically fix the heat block. There are two parts of the frame shown here, sometimes referred to herein as Frame Alpha and Frame Beta.

FIG. 8 section A provides a perspective view of sub-frame 410 (also referred to as Frame Alpha), while FIG. 8 section B provides a perspective view of sub-frame 420 (also referred to as Frame Beta). Section C of FIG. 8 shows sub-frame 420 positioned proximal to sub-frame 410 to form frame 450. Both of the frames comprise three major components: a base, a main structural carrier, and a press bar. The base is used for connection and fixation between the whole frame and the sliding platform. FIG. 8 section A illustrates sub-frame 410 with base 411 and main structural carrier 412, while FIG. 8 section B illustrates sub-frame 420 with base 421 and main structural carrier 422. FIG. 9 section A illustrates press bars 413 and 414 for use in conjunction with sub-frame 410, as well as press bars 423 and 424 for use in conjunction with sub-frame 420. In addition, FIG. 9 section A illustrates heat blocks 415 and 416 coupled to press bars 413 and 414, as well as heat blocks 425 and 426 coupled to press bars 423 and 424. FIG. 9 section B illustrates frame 450 with sub-components assembled. For purposes of clarity, not all individual components are labeled in section B.

The main structural carriers 412 and 422 play the main role in frame 450, and their primary function is to fix press bars 413, 414, 423 and 424 on claws 417 and 427 (labeled in FIG. 8 sections A and B). In certain embodiments, during manufacturing bases 411 and 421 and structural carriers 412 and 422 can be made as a single part, respectively. Each component can be produced from hard materials in order to maintain their shapes and forms. In 3D print prototyping, polylactic acid (PLA) material and acrylonitrile butadiene styrene (ABS) material, etc. can be suitable materials.

The function of press bars 413, 414, 423 and 424 is to fix heat blocks 415, 416, 425 and 426. As shown in FIG. 9 the shape of press bars 413, 414, 423 and 424 is an oblate U-shape. The press bar needs to maintain its shape at high temperatures, a heat resistant material is suggested. In the certain embodiments, polycarbonate (PC) or ceramic materials can be used for the press bars.

After coupling press bars 413, 414, 423 and 424 to frame 450 (via sub-frames 410 and 420), heat blocks 415, 416, 425 and 426 will be positioned vertically erect. Sub-frame 410 will assemble the front two heat blocks 415 and 416, and sub-frame 420 will assemble the back two heat blocks 425 and 426. The configuration (e.g. shape and dimensions) of sub-frames 410 and 420 (also referred to as Frame Alpha and Frame Beta) are different to facilitate nesting the two fully assembled sub-frames. As shown in FIG. 8, a linear actuator 430 is coupled between sub-frame 410 and sub-frame 420. When linear actuator 430 elongates, heat blocks 425 and 426 will move closer to heat blocks 415 and 416 until the heat blocks fully engage or clamp chip 100. When linear actuator 430 shortens, heat blocks 425 and 426 will move away from heat blocks 415 and 416 until the heat blocks successfully disengage or un-clamp chip 100.

Figure 10:
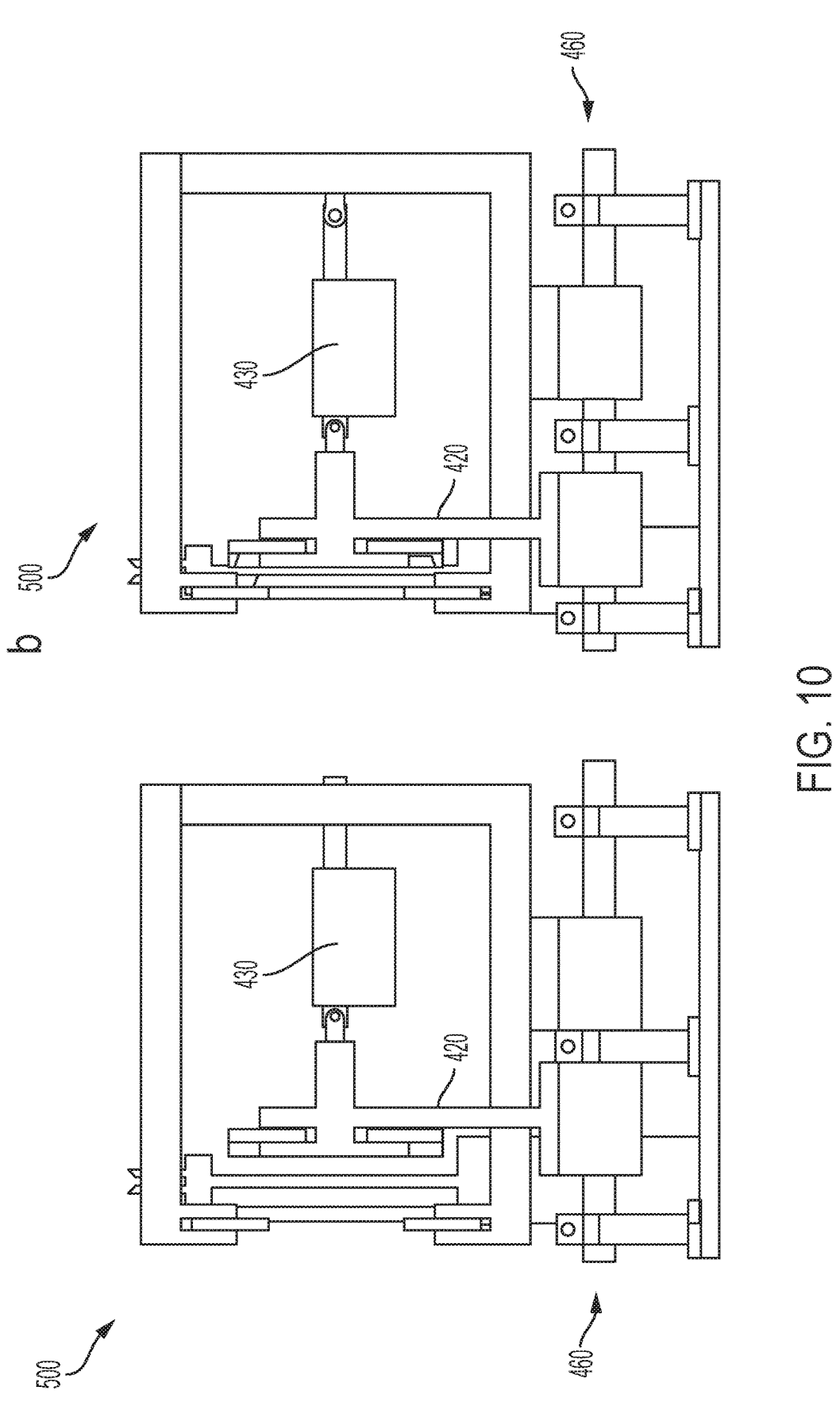
FIG. 10 illustrates the mechanical system of an apparatus according to the present disclosure in unclamped and clamped positions.
Figure 10:
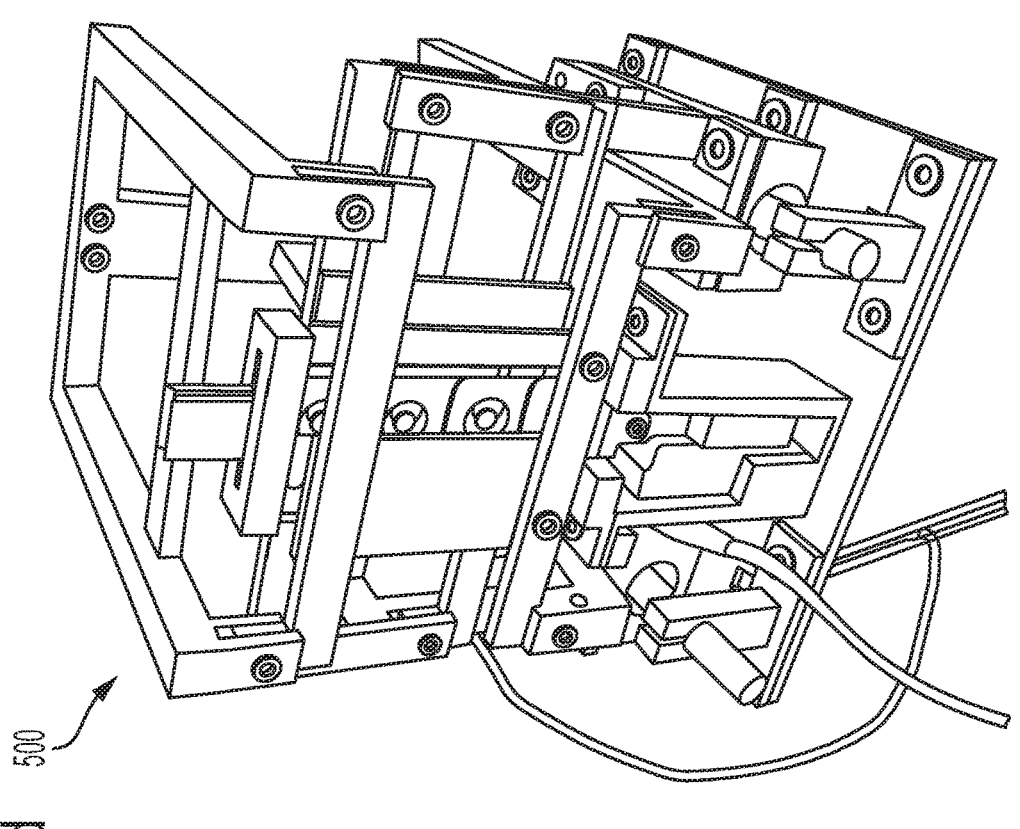
Figure 10:
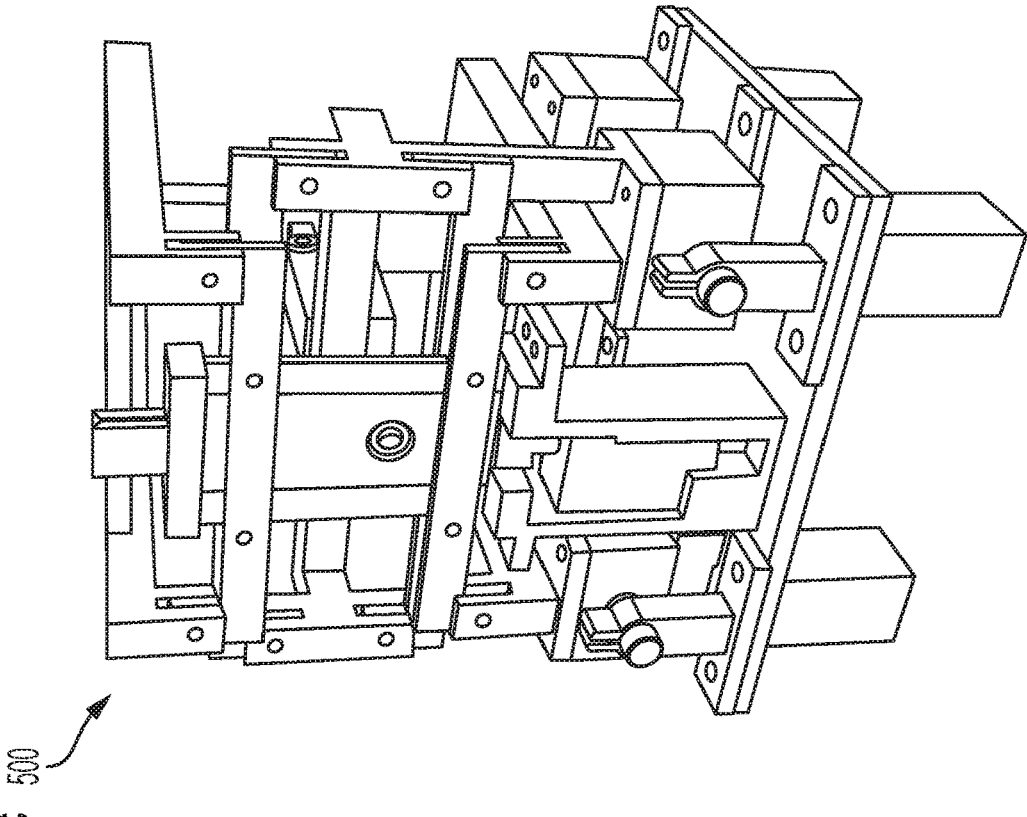

FIG. 10 provides an overview of mechanical system 500 configured to provide vertical loading and clamping of chip 100. Section A of FIG. 10 illustrates a side view of mechanical system 500 in an unclamped position. In this view, linear actuator 430 is in a retracted position and sub-frame 420 is moved toward linear actuator 430.

Section B of FIG. 10 illustrates a side view of mechanical system 500 in a clamped position. In this view, linear actuator 430 is in an extended position and sub-frame 420 is moved away from linear actuator 430 and toward chip 100.

Section C of FIG. 10 provides a perspective view of mechanical system 500 in the clamped position, while Section D provides a photograph of mechanical system 500 with a loaded Donut PCR chip 100. For purposes of clarity, not all components in FIG. 10 are labeled with reference numbers.

Sub-frames 410 and 420 can be supported with a sliding component 460 to facilitate frame movement forwards and backwards. In specific embodiments, a commercially available linear bearing platform (identified by component number SC8UU) can be used for the sliding component. In certain embodiments, the sliding component can include a sliding platform, a sliding bar, and a clamp stand. The surface of sliding platform is horizontal and coupled to frame bases 411 and 421. The sliding platform is coupled to the sliding bar and can move back and forth along the sliding bar.

In exemplary embodiments, the sliding platform design can be customized, as long as it maintains its function to minimize friction. In one embodiment, the sliding bar is a stainless-steel, surface-glazed cylinder with a diameter of 8 mm. In certain embodiments, two sliding bars can be used for the platform. The sliding bars can be chosen from many commercially available products, and can be any of a variety of dimensions and materials. The clamp stand is used for fixing and locating the sliding bar. In certain embodiments, three sets of clamp stands can be used, with each set containing two clamp stands. One set of clamp stands forms a partition and buffer between the two sets of sliding platforms for the purpose of prohibiting excessive movement, in order to avoid breaking the Donut PCR chip 100 during the clamping process.

Figure 11:
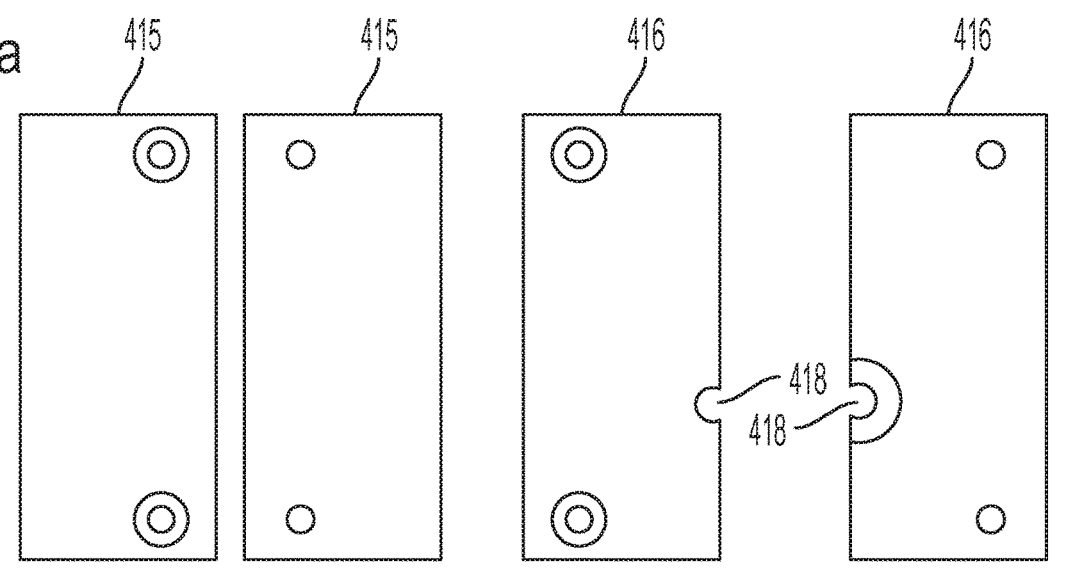
FIG. 11 illustrates orthographic and perspective representations of heat blocks individually and in an assembled frame of an apparatus according to the present disclosure.
Figure 11:
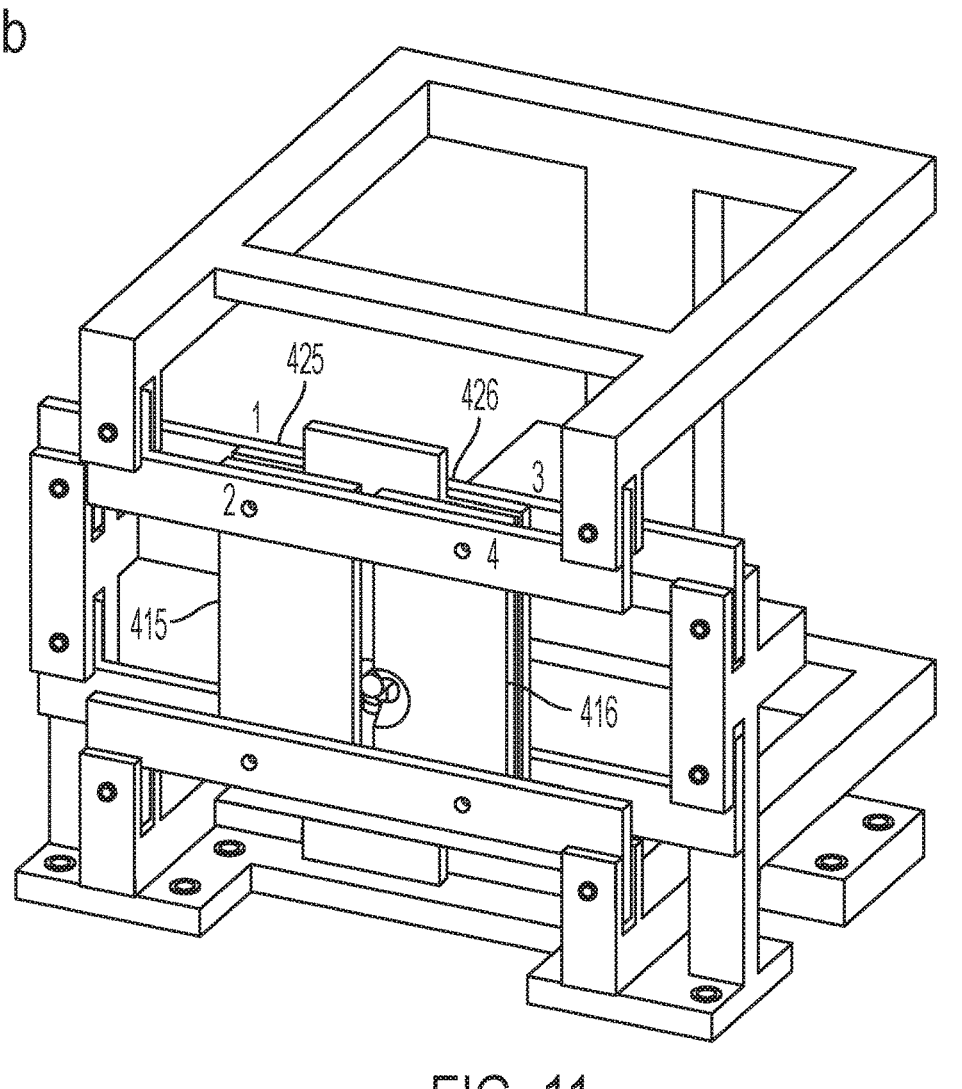

Exemplary embodiments of the present invention also comprise a thermal control system configured to maintain two different temperatures of chip 100 via heat blocks 415, 416, 425 and 426. Referring now to FIG. 11 section A, front and back views are provided for heat blocks 415 and 416. As shown in FIG. 11, heat block 416 comprises a tapered aperture 418 proximal to one edge of block 416. As described further below, tapered aperture 418 allows for fluorescent imaging. The center of tapered aperture 418 corresponds to the position of the label-free microarray on the loaded Donut PCR chip 100 when heat block 416 is in the clamped position. In the embodiment shown, heat blocks

415 and 425 are set at 95° C. during operation, and heat blocks 416 and 426 are set at 60° C. during operation.

Figure 12:
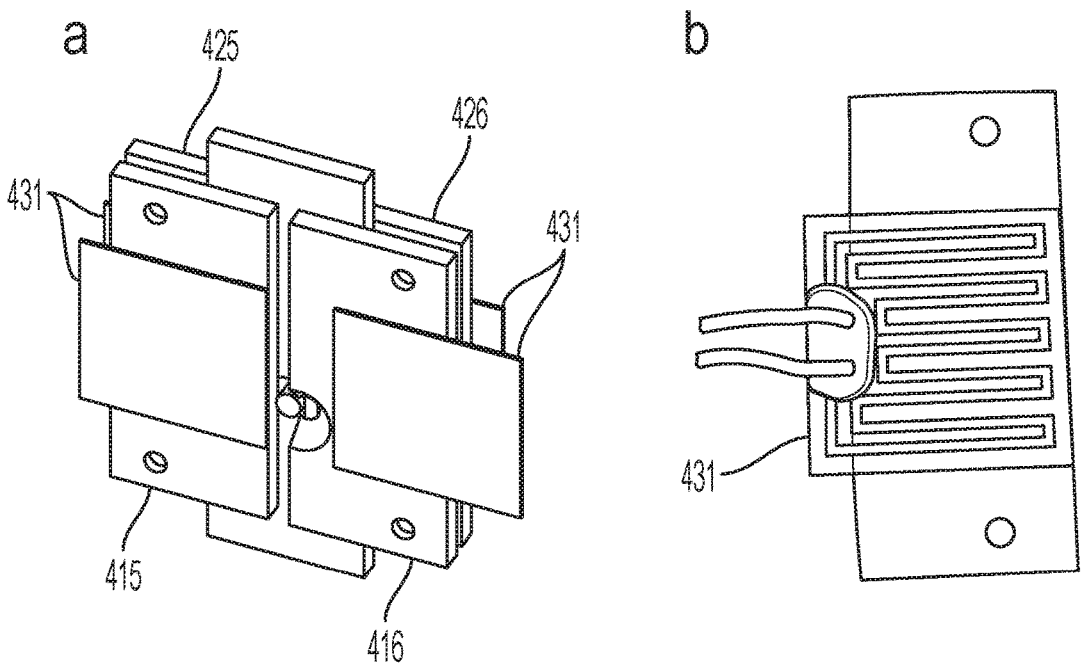
FIG. 12 illustrates orthographic, perspective and photographic representations of thermal control system components of an apparatus according to the present disclosure, as well as a response curve of heat block temperature.
Figure 12:
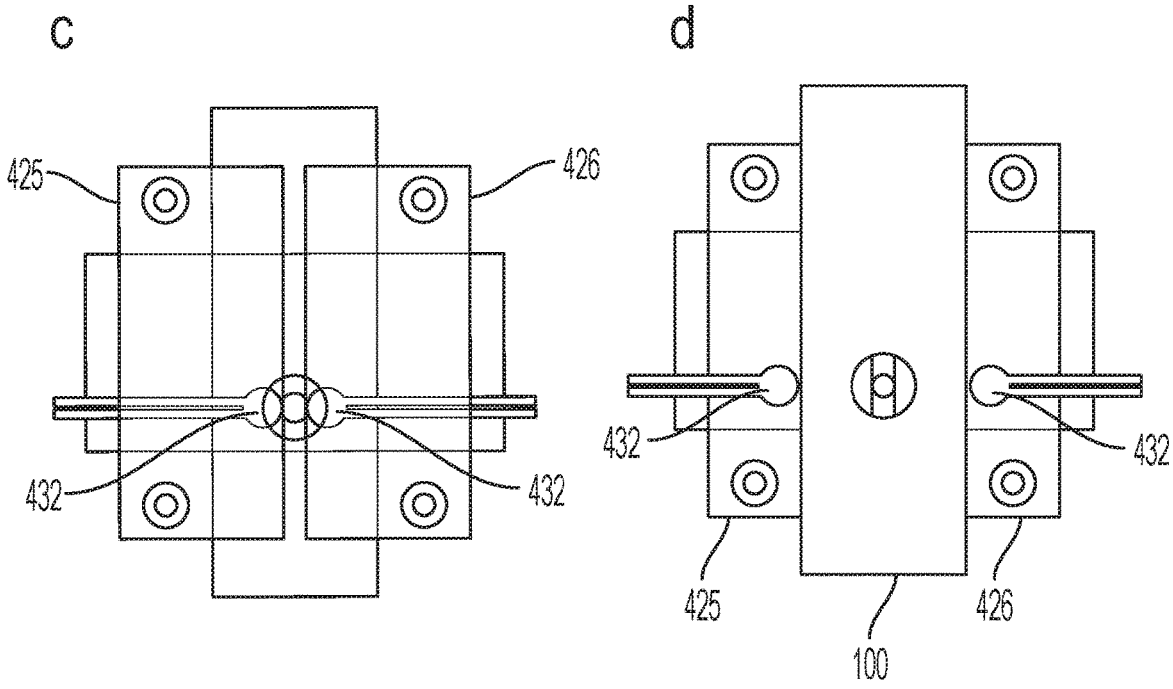
Figure 12:
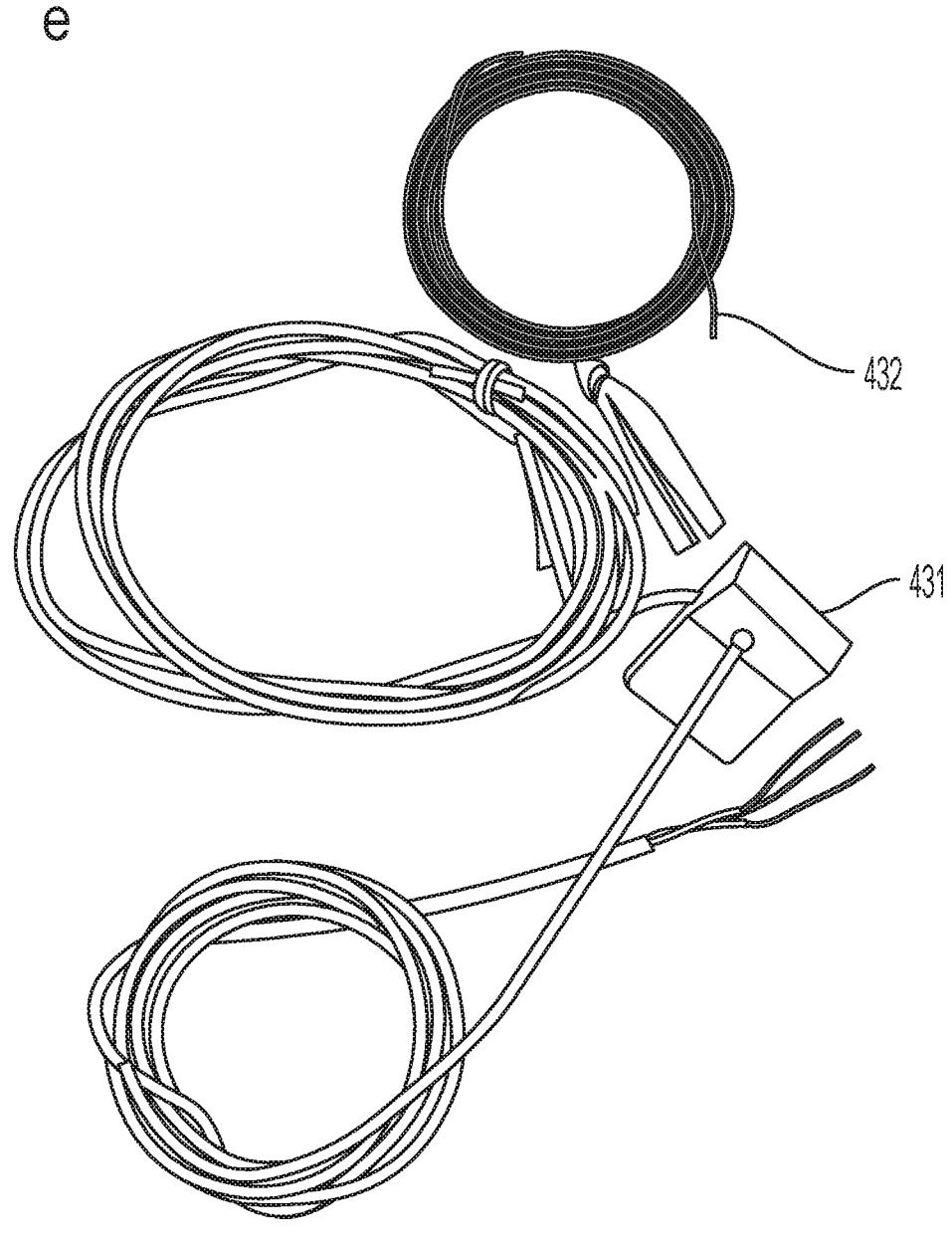
Figure 12:
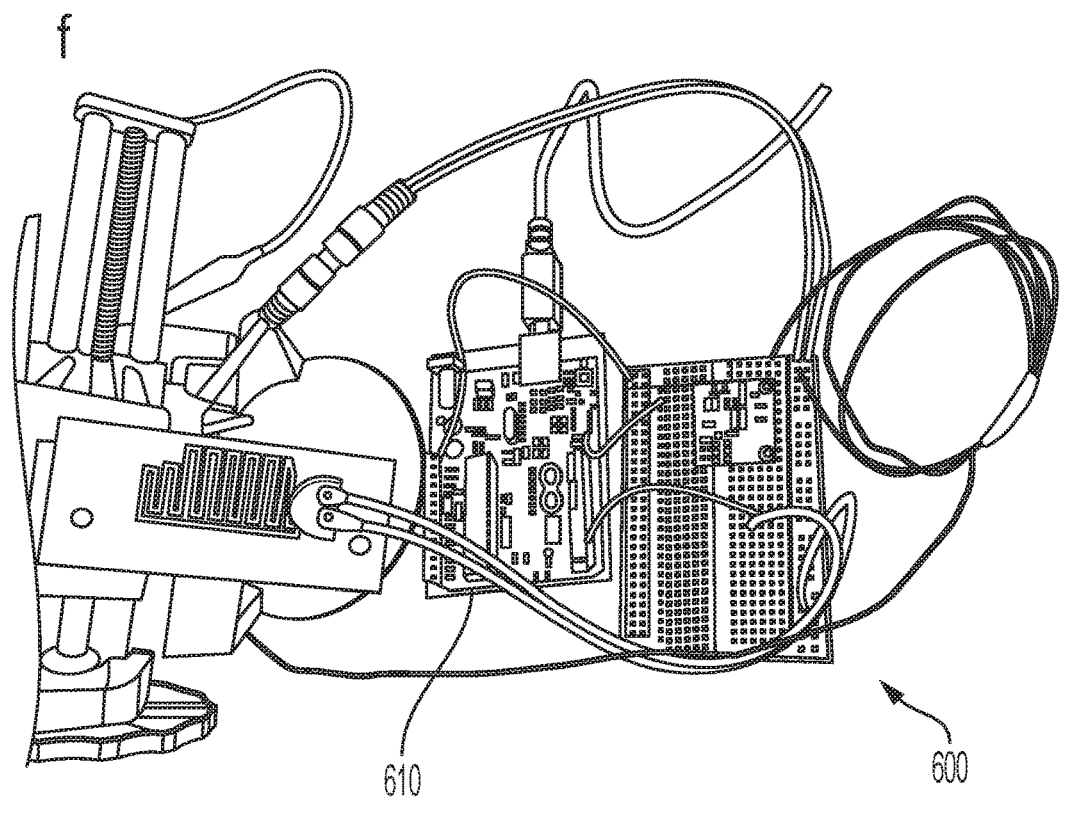
Figure 12:
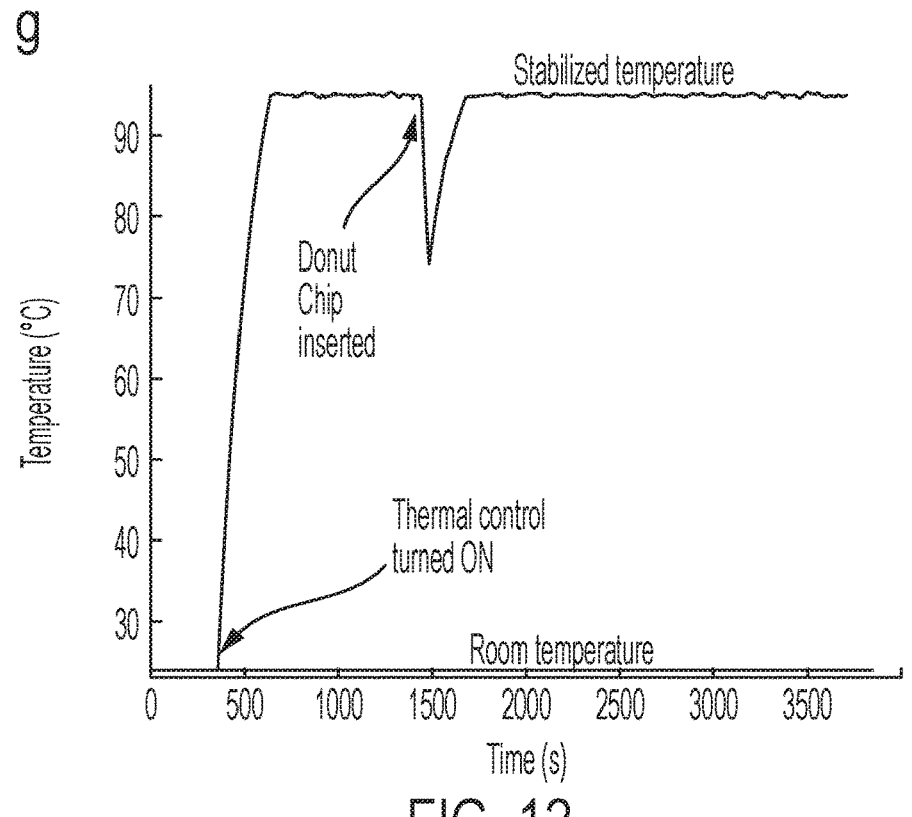

FIG. 12 illustrates different aspects of exemplary embodiments of a thermal control system according to the present invention. Section A illustrates a schematic perspective view of 3-D diagram of heat sources 431 attached to heat blocks, while section B provides a photograph of a heat sources 431 configured as an adhesive flexible heater coupled to a heater block (e.g. block 426). FIG. 12 section C illustrates a partial section view of a temperature sensor 432 embedded in heat block 425 and 426 underneath the Donut PCR chip chamber. FIG. 12 section D illustrates temperature sensors 432 attached beside chip 100 and on the surface of heat block 425 and 426. Section E of FIG. 12 provides a photograph of a temperature sensors 432 configured as a thermocouple and thermistor. In addition, FIG. 12 section E shows a variety of temperature sensors, including a surface adhesive RTD sensor. Section F of FIG. 12 provides a photograph of a thermal control system 600, including a prototype of a thermal control board 610. FIG. 12 section G illustrates a response curve of heat block temperature measured in degrees Celsius versus time in seconds.

In certain exemplary embodiments, the heat block is a heating conductive board with a glazed surface. In particular embodiments, the heat block should exhibit a width and length that can cover at least half of the Donut PCR chip. The principle of the heat block is to heat the chip to predetermined temperature through clamping the chip onto the glazed surface of the heated heat block. In the specific embodiment shown in the figures, a total of four individual heat blocks are used. During operation of the instrument, two of the heat blocks maintain a 95° C. temperature, and two maintain a 60° C. temperature.

The total number of heat blocks used for stable temperature control can vary. For example, in FIG. 11, the use of only heaters 415 and 416 may be sufficient given a good feedback control loop for maintaining temperature. In the embodiment shown in the figures, four heat blocks are used for temperature robustness and fault tolerance. The material used in the heat block could be aluminum, stainless steel, or brass or other suitable material for heat conduction. The thickness of the heat block can be adjusted based on the desired temperature and the properties of the heat sources. In the exemplary embodiment shown in the figures, three-millimeter thick aluminum boards are used for the heat blocks.

In exemplary embodiments, the temperature sensor can be assembled either on the surface of the heat block or be embedded in the heat block, as shown in FIG. 12 sections C and D. In the illustrated embodiment, the temperature sensors are embedded in the heat blocks at the positions where the heat block contacts the Donut PCR chip, in order to achieve the most accurate temperature readings of the Donut PCR chip temperature (see FIG. 12 section C). In exemplary embodiments, the temperature sensor should be capable of accurately measuring temperatures from 20° C. to 105° C., with a response time ≤1 second, and accuracy ≤1.5° C. The embodiment shown in the figures utilized an OMEGA Thermocouple Type-T. Experimentally, it has been observed that other types of thermocouple achieve similar results. Alternatively, resistance temperature detector (RTD) or thermistor can be used instead. Note that the heat block's shape should accommodate the shape of the temperature sensor, if applying an embedded temperature sensor strategy.

Exemplary embodiments of the present disclosure also comprise a heat source that provides heat to the heat blocks.

The illustrated embodiments include a Kapton Polyimide adhesive flexible heater. This heater adheres to the heat block surface, but does not directly contact the Donut PCR chip. The heater maintains the temperature through changing the power provided to the heat source. Alternatively, any heating plate that contains a heating wire can replace the heat block or heater. Specifically, it is noted that the heat source can provide rapid heating of the heat blocks via conversion of electrical energy to heat, but cannot provide rapid cooling.

Exemplary embodiments further comprise a temperature sensor feedback loop as a central aspect of the thermal controller. The thermal controller reads the temperature from a temperature sensor and provides guidance on the power to the heat block to (1) rapidly implement heating to the desired temperature, and (2) to accurately maintain the temperature despite potential fluctuations due to environment. Exemplary embodiments can use an Arduino Microcontroller to accurately read the temperature of the thermocouple through an amplifier module, and to control the power of heat source. Alternatively, a general PID (proportional-integral-derivative) controller is capable of achieving the same function.

Figure 13:
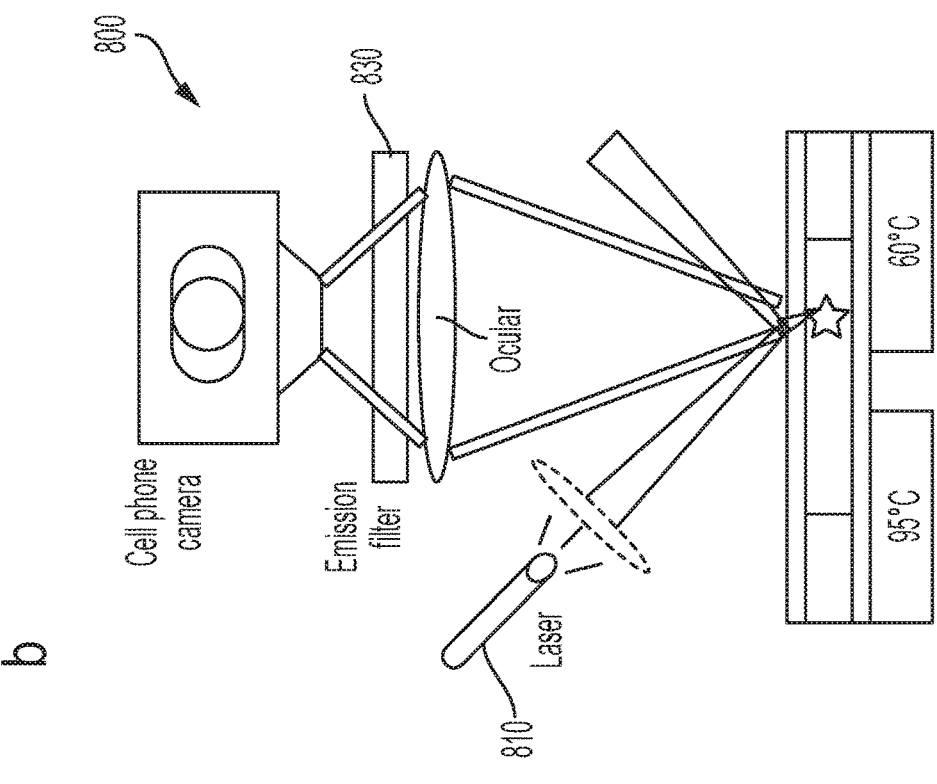
FIG. 13 illustrates schematic representations of fluorescence imaging systems of an apparatus according to the present disclosure.
Figure 13:
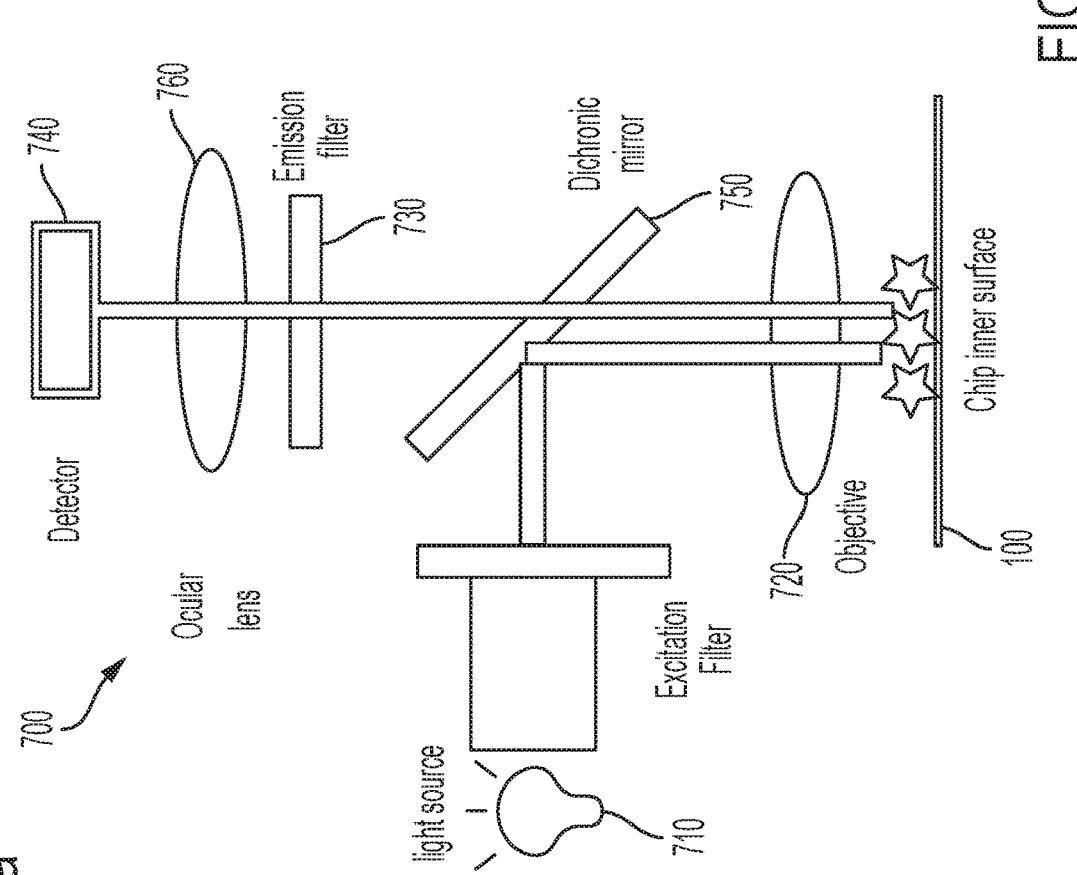

Exemplary embodiments of the present invention also comprise an optical fluorescence imaging system configured to collect spatial information in an array of at least 40 pixels by 40 pixels. Referring now to FIG. 13, an overview of exemplary optical fluorescence imaging systems is shown. Section A of FIG. 13 illustrates a system 700 including a traditional or typical fluorescence microscope arrangement, while section B illustrates a schematic diagram of an optics system 800 used for a prototype instrument.

Fluorescence imaging of the Donut PCR chip 100 requires a light source 710, an optical module 720 to guide and focus the light to the appropriate region of chip 100, an emission filter 730 to reduce background signal in other wavelengths, and a photodetector array 740 or camera for image acquisition.

In the embodiment shown in FIG. 13 section A, system 700 also comprises a dichroic mirror 750, which is a high-pass mirror that will reflect shorter wavelength light, while allowing longer wavelength light to pass through. Therefore, excitation light will be reflected to specimen to pass through objectives and then excite the fluorophore. The emitted photons are red-shifted by roughly 20 nm, and will pass through dichroic mirror 750. To improve signal-to-noise ratio, emission filter 730 is applied to block background light of other wavelengths. Finally, emission light passes through an ocular lens 760 for better magnification and focusing.

The above describes a standard method for fluorescence imaging used in fluorescence microscopes. Section B of FIG. 13 presents a simplified alternative design of system 800 that is more portable and compatible with a smartphone camera. System 800 uses only one emission filter 830 and one green light laser (532 nm) 810. In the embodiment shown, the green laser 810 serves as a coherent light source, and is pointed at 45° C. angle relative to the chip surface. The DNA microarray can be clearly visualized through emission filter 830. Alternative light sources (e.g. a light-emitting diode (LED) or arc lamp) can be used instead of a laser, but would require an additional excitation filter and would need to be focused.

Referring back now section A of FIG. 13, optical lens 760 is used to provide magnification. Either a scientific camera or a cell phone camera can yield a clear microarray image for downstream image processing by specialized software.

The image shown in section E of FIG. 2 was taken using a scientific camera with standard filter sets. The image in section C of FIG. 4 was taken using iPhone 6s using the setup shown in section B of FIG. 12. Alternatively, a properly positioned array of photodetectors may also function to provide the relevant information on the microarray spot brightness.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.
PCT Patent Publication WO 2017/172760

The invention claimed is:

1. A method comprising:
(a) providing a chip between a first block at a first temperature forming a first temperature zone and a second block at a second temperature forming a second temperature zone that is distinct from the first temperature;
(b) providing an excitation light to a surface of the chip;
(c) detecting an emitted light from the chip; and
(d) analyzing a sample in the chip from processing the emitted light during a predetermined sampling, wherein:
the chip comprises an annular member;
the chip is injected with PCR solution comprising an aqueous solution configured to controllably and uniformly circulate as a result of a temperature-induced density difference between the first temperature zone and the second temperature zone;
the chip is loaded, vertically positioned and actively secured between the first block and the second block by a mechanical system;
the mechanical system is configured to actively secure the chip in response to loading the chip so that at least 50 percent of a total surface area of the annular member is in contact with the first block and the second block collectively to form thermal contacts between the chip and the respective blocks having the respective temperature zones; and
analyzing the sample in the chip from processing the emitted light comprises collecting spatial information in an array of at least 40 pixels×40 pixels by an optical fluorescence imaging system.
2. The method of claim 1, wherein one of the first temperature and the second temperature is from 75° C. to 105° C.

3. The method of claim 1, wherein one of the first temperature and the second temperature is from 30° C. to 75° C.

4. The method of claim 1, wherein, in (a), the first and second temperatures are controlled by a microcontroller program that alters a heat source power based on feedback from a temperature sensor.

5. The method of claim 1, wherein, in (a), the first and second temperatures are controlled by a proportional-integral-derivative (PID) controller.

6. The method of claim 1, wherein the first block comprises a first temperature sensor.

7. The method of claim 1, wherein the second block comprises a second temperature sensor.

8. The method of claim 1, wherein a surface of the first block is coupled to a first temperature sensor.

9. The method of claim 1, wherein a surface of the second block is coupled to a second temperature sensor.

10. The method of claim 1, comprising, prior to (a), loading the chip into an apparatus that comprises the first block and the second block.

11. The method of claim 10, wherein said loading comprises operating a motor for linear movement.

12. The method of claim 10, wherein said loading comprises operating a mechanism configured to draw the chip into the apparatus.

13. The method of claim 1, wherein said providing comprises clamping the chip between the first block and the second block.

14. The method of claim 13, wherein said clamping comprises operating a mechanism with a self-locking motor, a cam-follower combination, or a spring.

15. The method of claim 13, comprising, subsequent to (d), unclamping the chip from between the first block and the second block.

16. The method of claim 1, wherein, in (b), the excitation light forms an angle with the surface of the chip from 30° to 90°.

17. The method of claim 1, wherein, in (c), said detecting comprises operating a camera to acquire images continually with a frequency of no less than 1 image every 2 minutes.

18. The method of claim 1, wherein the surface of the chip comprises one or more microarrays that comprises a plurality of probes.

* * * * *